United States Patent
Wang et al.

(10) Patent No.: US 7,938,813 B2
(45) Date of Patent: May 10, 2011

(54) ABSORBENT ARTICLE HAVING SHAPED ABSORBENT CORE FORMED ON A SUBSTRATE

(75) Inventors: James H. Wang, Appleton, WI (US); Peter R. Elliker, Appleton, WI (US); Stacy A. Mundschau, Oshkosh, WI (US); James M. Kaun, Neenah, WI (US); Theodore T. Tower, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 240 days.

(21) Appl. No.: 10/880,996

(22) Filed: Jun. 30, 2004

(65) Prior Publication Data
US 2006/0009743 A1 Jan. 12, 2006

(51) Int. Cl.
*A61F 13/15* (2006.01)

(52) U.S. Cl. ..... 604/385.101; 604/385.01; 604/385.201; 604/385.21; 604/378

(58) Field of Classification Search ........... 604/367, 604/366, 365, 368, 370, 385.01, 385.101, 604/378, 385.201, 385.21
See application file for complete search history.

(56) References Cited

U.S. PATENT DOCUMENTS

| | | |
|---|---|---|
| 3,338,992 A | 8/1967 | Kinney |
| 3,339,546 A | 9/1967 | Chen |
| 3,341,394 A | 9/1967 | Kinney |
| 3,485,706 A | 12/1969 | Evans |
| 3,502,538 A | 3/1970 | Levy |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 3,855,046 A | 12/1974 | Hansen et al. |
| 3,901,236 A | 8/1975 | Assarsson et al. |
| 3,966,865 A | 6/1976 | Nishida et al. |
| 4,055,180 A | 10/1977 | Karami |
| 4,076,663 A | 2/1978 | Masuda et al. |
| 4,100,324 A | 7/1978 | Anderson et al. |
| 4,286,082 A | 8/1981 | Tsubakimoto et al. |
| 4,340,563 A | 7/1982 | Appel et al. |
| 4,369,156 A | 1/1983 | Mathes et al. |
| 4,427,737 A | 1/1984 | Cilento et al. |

(Continued)

FOREIGN PATENT DOCUMENTS
EP 0 315 507 A2 5/1989
(Continued)

OTHER PUBLICATIONS

American Society for Testing Materials (ASTM) Designation: D1238-70, "Standard Method for Measuring Flow Rates of Thermoplastics by Extrusion Plastometer," pp. 415-426.

(Continued)

*Primary Examiner* — Jacqueline F. Stephens
(74) *Attorney, Agent, or Firm* — Armstrong Teasdale LLP

(57) ABSTRACT

An absorbent article includes a stretchable substrate layer and an absorbent core formed directly on the substrate layer, and adhesively attached to the substrate layer. The absorbent core includes about 40-99% by weight superabsorbent particles and about 1-60% by weight adhesive fibers. The absorbent core does not prevent the substrate layer or absorbent article from stretching. The absorbent article can be a personal care absorbent article or a medical absorbent article, and is suitably stretchable or elastic in at least one direction.

45 Claims, 8 Drawing Sheets

U.S. PATENT DOCUMENTS

| | | |
|---|---|---|
| 4,429,001 A | 1/1984 | Kolpin et al. |
| 4,469,734 A | 9/1984 | Minto et al. |
| 4,488,928 A | 12/1984 | Khan et al. |
| 4,530,353 A | 7/1985 | Lauritzen |
| 4,542,199 A | 9/1985 | Kaminsky et al. |
| 4,547,420 A | 10/1985 | Krueger et al. |
| 4,551,191 A | 11/1985 | Kock et al. |
| 4,587,154 A | 5/1986 | Hotchkiss et al. |
| 4,588,630 A | 5/1986 | Shimalla |
| 4,604,313 A | 8/1986 | McFarland et al. |
| 4,654,038 A | 3/1987 | Sakurai |
| 4,655,757 A | 4/1987 | McFarland et al. |
| 4,704,116 A | 11/1987 | Enloe |
| 4,724,114 A | 2/1988 | McFarland et al. |
| 4,729,371 A | 3/1988 | Krueger et al. |
| 4,767,825 A | 8/1988 | Pazos et al. |
| 4,775,579 A | 10/1988 | Hagy et al. |
| 4,795,668 A | 1/1989 | Krueger et al. |
| 4,803,117 A | 2/1989 | Daponte |
| 4,806,408 A | 2/1989 | Pierre et al. |
| 4,818,464 A | 4/1989 | Lau |
| 4,834,738 A | 5/1989 | Kielpikowski et al. |
| 4,865,596 A | 9/1989 | Weisman et al. |
| 4,879,170 A | 11/1989 | Radwanski et al. |
| 4,891,258 A | 1/1990 | Fahrenkrug |
| 4,904,440 A | 2/1990 | Angstadt |
| 4,923,914 A | 5/1990 | Nohr et al. |
| 4,939,016 A | 7/1990 | Radwanski et al. |
| 4,940,464 A | 7/1990 | Van Gompel et al. |
| 4,957,795 A | 9/1990 | Riedel |
| 4,996,091 A | 2/1991 | McIntyre |
| 5,057,166 A | 10/1991 | Young, Sr. et al. |
| 5,064,689 A | 11/1991 | Young, Sr. et al. |
| 5,064,802 A | 11/1991 | Stevens et al. |
| 5,108,820 A | 4/1992 | Kaneko et al. |
| 5,114,781 A | 5/1992 | Morman |
| 5,116,662 A | 5/1992 | Morman |
| 5,143,680 A | 9/1992 | Molnar et al. |
| 5,149,335 A | 9/1992 | Kellenberger et al. |
| 5,169,706 A | 12/1992 | Collier, IV et al. |
| 5,171,391 A | 12/1992 | Chmielewski et al. |
| 5,188,624 A | 2/1993 | Young, Sr. et al. |
| 5,189,192 A | 2/1993 | LaPointe et al. |
| 5,204,429 A | 4/1993 | Kaminsky et al. |
| 5,213,881 A | 5/1993 | Timmons et al. |
| 5,225,014 A | 7/1993 | Ogata et al. |
| 5,230,959 A | 7/1993 | Young, Sr. et al. |
| 5,248,524 A | 9/1993 | Soderlund |
| 5,260,126 A | 11/1993 | Collier, IV et al. |
| 5,272,236 A | 12/1993 | Lai et al. |
| 5,278,272 A | 1/1994 | Lai et al. |
| 5,279,854 A | 1/1994 | Kendall et al. |
| 5,281,207 A | 1/1994 | Chmielewski et al. |
| 5,284,703 A | 2/1994 | Everhart et al. |
| 5,288,791 A | 2/1994 | Collier, IV et al. |
| 5,290,626 A | 3/1994 | Nishiol et al. |
| 5,302,447 A | 4/1994 | Ogata et al. |
| 5,308,906 A | 5/1994 | Taylor et al. |
| 5,332,613 A | 7/1994 | Taylor et al. |
| 5,336,552 A | 8/1994 | Strack et al. |
| 5,349,100 A | 9/1994 | Mintz |
| 5,350,597 A | 9/1994 | Pelley |
| 5,350,624 A | 9/1994 | Georger et al. |
| 5,352,749 A | 10/1994 | Dechellis et al. |
| 5,366,793 A | 11/1994 | Fitts, Jr. et al. |
| 5,372,885 A | 12/1994 | Tabor et al. |
| 5,374,696 A | 12/1994 | Rosen et al. |
| 5,376,198 A | 12/1994 | Fahrenkrug et al. |
| 5,382,400 A | 1/1995 | Pike et al. |
| 5,385,775 A | 1/1995 | Wright |
| 5,387,208 A | 2/1995 | Ashton et al. |
| 5,389,202 A | 2/1995 | Everhart et al. |
| 5,411,497 A | 5/1995 | Tanzer et al. |
| 5,421,940 A | 6/1995 | Cornils et al. |
| 5,424,115 A | 6/1995 | Stokes |
| 5,425,725 A | 6/1995 | Tanzer et al. |
| 5,432,000 A | 7/1995 | Young, Sr. et al. |
| 5,433,715 A | 7/1995 | Tanzer et al. |
| 5,486,166 A | 1/1996 | Bishop et al. |
| 5,490,846 A | 2/1996 | Ellis et al. |
| 5,503,908 A | 4/1996 | Faass |
| 5,508,102 A | 4/1996 | Georger et al. |
| 5,509,915 A | 4/1996 | Hanson et al. |
| 5,511,960 A | 4/1996 | Terakawa et al. |
| 5,516,585 A | 5/1996 | Young, Sr. et al. |
| 5,518,801 A | 5/1996 | Chappell et al. |
| 5,560,878 A | 10/1996 | Dragoo et al. |
| 5,562,645 A | 10/1996 | Tanzer et al. |
| 5,567,472 A | 10/1996 | Siegfried et al. |
| 5,593,399 A | 1/1997 | Tanzer et al. |
| 5,601,542 A | 2/1997 | Melius et al. |
| 5,614,283 A | 3/1997 | Potnis et al. |
| 5,645,542 A | 7/1997 | Anjur et al. |
| 5,670,044 A | 9/1997 | Ogata et al. |
| 5,676,660 A | 10/1997 | Mukaida et al. |
| 5,679,042 A | 10/1997 | Varona |
| 5,681,305 A | 10/1997 | Korpman |
| 5,683,752 A | 11/1997 | Popp et al. |
| 5,691,035 A | 11/1997 | Chappell et al. |
| 5,713,881 A | 2/1998 | Rezai et al. |
| 5,718,913 A | 2/1998 | Dhuique-Mayer et al. |
| 5,720,832 A | 2/1998 | Minto et al. |
| 5,759,926 A | 6/1998 | Pike et al. |
| 5,766,389 A | 6/1998 | Brandon et al. |
| 5,789,065 A | 8/1998 | Haffner et al. |
| 5,820,973 A | 10/1998 | Dodge, II et al. |
| 5,824,004 A | 10/1998 | Osborn, III et al. |
| 5,833,678 A | 11/1998 | Ashton et al. |
| 5,849,000 A | 12/1998 | Anjur et al. |
| 5,853,881 A | 12/1998 | Estey et al. |
| 5,858,292 A | 1/1999 | Dragoo et al. |
| 5,858,515 A | 1/1999 | Stokes et al. |
| 5,879,751 A | 3/1999 | Bogdanski |
| 5,882,769 A | 3/1999 | McCormack et al. |
| 5,883,028 A | 3/1999 | Morman et al. |
| 5,891,120 A | 4/1999 | Chmielewski |
| 5,900,109 A | 5/1999 | Sanders et al. |
| 5,904,675 A | 5/1999 | Laux et al. |
| 5,922,163 A | 7/1999 | Helynranta et al. |
| 5,938,650 A | 8/1999 | Baer et al. |
| 5,964,743 A | 10/1999 | Abuto et al. |
| 5,977,014 A | 11/1999 | Plischke et al. |
| 5,981,410 A | 11/1999 | Hansen et al. |
| 5,981,689 A | 11/1999 | Mitchell et al. |
| 5,994,440 A | 11/1999 | Staples et al. |
| 6,046,377 A | 4/2000 | Huntoon et al. |
| 6,060,115 A | 5/2000 | Borowski et al. |
| 6,068,620 A | 5/2000 | Chmielewski |
| 6,072,101 A | 6/2000 | Beihoffer et al. |
| 6,080,909 A | 6/2000 | Österdahl et al. |
| 6,087,448 A | 7/2000 | Mitchell et al. |
| 6,090,875 A | 7/2000 | Staples et al. |
| 6,121,409 A | 9/2000 | Mitchell et al. |
| 6,129,720 A | 10/2000 | Blenke et al. |
| 6,159,591 A | 12/2000 | Beihoffer et al. |
| 6,194,631 B1 | 2/2001 | Mitchell et al. |
| 6,221,062 B1 | 4/2001 | Osborn, III |
| 6,222,091 B1 | 4/2001 | Beihoffer et al. |
| 6,231,557 B1 | 5/2001 | Krautkramer et al. |
| 6,235,965 B1 | 5/2001 | Beihoffer et al. |
| 6,241,713 B1 | 6/2001 | Gross et al. |
| 6,261,679 B1 | 7/2001 | Chen et al. |
| 6,290,686 B1 | 9/2001 | Tanzer |
| 6,342,298 B1 | 1/2002 | Evans et al. |
| 6,353,148 B1 | 3/2002 | Gross |
| 6,362,389 B1 | 3/2002 | McDowall et al. |
| 6,376,072 B1 | 4/2002 | Evans et al. |
| 6,387,495 B1 | 5/2002 | Reeves et al. |
| 6,392,116 B1 | 5/2002 | Beihoffer et al. |
| 6,403,857 B1 | 6/2002 | Gross et al. |
| 6,429,350 B1 | 8/2002 | Tanzer et al. |
| 6,455,114 B1 | 9/2002 | Goldhirsch et al. |
| 6,455,753 B1 | 9/2002 | Glaug et al. |
| 6,470,943 B1 | 10/2002 | Borowski et al. |
| 6,509,512 B1 | 1/2003 | Beihoffer et al. |
| 6,509,513 B2 | 1/2003 | Glaug et al. |
| 6,552,245 B1 | 4/2003 | Roessler et al. |

| | | | | | | |
|---|---|---|---|---|---|---|
| 6,555,502 | B1 | 4/2003 | Beihoffer et al. | WO | WO 96/16624 A2 | 6/1996 |
| 6,579,274 | B1 | 6/2003 | Morman et al. | WO | 97/39780 | 10/1997 |
| 6,582,413 | B2 | 6/2003 | Krautkramer et al. | WO | WO 98/03710 A1 | 1/1998 |
| 6,590,138 | B2 | 7/2003 | Onishi | WO | WO 98/45519 A1 | 10/1998 |
| 6,603,054 | B2 | 8/2003 | Chen et al. | WO | WO 99/00093 A1 | 1/1999 |
| 6,605,552 | B2 | 8/2003 | Jackson et al. | WO | WO 99/00095 A1 | 1/1999 |
| 6,610,900 | B1 | 8/2003 | Tanzer | WO | 99/25393 | 5/1999 |
| 6,627,564 | B1 | 9/2003 | Morman et al. | WO | 99/25745 | 5/1999 |
| 6,641,134 | B1 | 11/2003 | Dobbertin et al. | WO | 99/25748 | 5/1999 |
| 6,641,695 | B2 | 11/2003 | Baker | WO | 00/37000 | 6/2000 |
| 6,645,190 | B1 | 11/2003 | Olson et al. | WO | WO 00/37009 A2 | 6/2000 |
| 6,965,058 | B1 | 11/2005 | Raidel et al. | WO | WO 00/37735 A1 | 6/2000 |
| 7,270,889 | B2 * | 9/2007 | Campbell et al. ............ 428/516 | WO | 00/56959 | 9/2000 |
| 2001/0001312 | A1 | 5/2001 | Mitchell et al. | WO | 00/59439 | 10/2000 |
| 2001/0007064 | A1 | 7/2001 | Mitchell et al. | WO | 00/63295 | 10/2000 |
| 2001/0029358 | A1 | 10/2001 | Beihoffer et al. | WO | 01/15650 | 3/2001 |
| 2001/0044612 | A1 | 11/2001 | Beihoffer et al. | WO | 02/10032 | 2/2002 |
| 2002/0007166 | A1 | 1/2002 | Mitchell et al. | WO | 02/24132 | 3/2002 |
| 2002/0015846 | A1 | 2/2002 | Evans et al. | WO | 02/34184 | 5/2002 |
| 2002/0095127 | A1 | 7/2002 | Fish et al. | WO | WO 02/43784 A2 | 6/2002 |
| 2002/0150761 | A1 | 10/2002 | Lange et al. | WO | 02/053378 | 7/2002 |
| 2002/0183703 | A1 | 12/2002 | Singh et al. | WO | 03/018671 | 3/2003 |
| 2003/0014027 | A1 | 1/2003 | Beihoffer et al. | WO | 03/037392 | 5/2003 |
| 2003/0060112 | A1 | 3/2003 | Rezai et al. | WO | 03/047485 | 6/2003 |
| 2003/0105441 | A1 | 6/2003 | Chmielewski | WO | 03/051411 | 6/2003 |
| 2003/0114071 | A1 | 6/2003 | Everhart et al. | WO | 03/051417 | 6/2003 |
| 2003/0116888 | A1 | 6/2003 | Rymer et al. | WO | 03/057964 | 7/2003 |
| 2003/0129915 | A1 | 7/2003 | Harriz | WO | 03053297 | 7/2003 |
| 2003/0134102 | A1 | 7/2003 | Wang et al. | WO | WO 03/053297 A2 | 7/2003 |
| 2003/0158531 | A1 | 8/2003 | Chmielewski | WO | WO 03/053319 A2 | 7/2003 |
| 2003/0171729 | A1 * | 9/2003 | Kaun et al. ............ 604/382 | WO | WO 03/057268 A1 | 7/2003 |
| 2004/0054341 | A1 | 3/2004 | Kellenberger et al. | WO | 03/068122 | 8/2003 |
| 2004/0116014 | A1 | 6/2004 | Soerens et al. | WO | WO 2005/044163 | 5/2005 |
| 2004/0116287 | A1 | 6/2004 | Wang et al. | WO | WO 2005/044163 A1 | 5/2005 |
| 2004/0222568 | A1 | 11/2004 | Armantrout et al. | | | |
| 2005/0096435 | A1 | 5/2005 | Smith et al. | | | |
| 2005/0096623 | A1 | 5/2005 | Nhan et al. | | | |
| 2005/0137085 | A1 | 6/2005 | Zhang et al. | | | |
| 2005/0186351 | A1 | 8/2005 | Fung et al. | | | |
| 2005/0228350 | A1 | 10/2005 | Ranganathan et al. | | | |
| 2006/0004336 | A1 | 1/2006 | Zhang et al. | | | |
| 2006/0005919 | A1 | 1/2006 | Schewe et al. | | | |

FOREIGN PATENT DOCUMENTS

| | | |
|---|---|---|
| EP | 0 333 209 A2 | 9/1989 |
| EP | 0 341 870 A2 | 11/1989 |
| EP | 0 179 937 B1 | 4/1990 |
| EP | 0 492 554 A1 | 7/1992 |
| EP | 0 497 072 | 8/1992 |
| EP | 0 534 863 A1 | 3/1993 |
| EP | 0 601 610 A1 | 6/1994 |
| EP | 0 633 009 | 1/1995 |
| EP | 0 700 672 A1 | 3/1996 |
| EP | 0 700 673 | 3/1996 |
| EP | 0 788 874 B1 | 9/1999 |
| EP | 0 947 549 A1 | 10/1999 |
| EP | 0 788 336 B1 | 6/2000 |
| EP | 1 013 291 | 6/2000 |
| EP | 0 994 686 B1 | 11/2002 |
| EP | 0 794 751 B2 | 1/2003 |
| EP | 0 802 949 B1 | 5/2003 |
| GB | 2 151 272 A | 7/1985 |
| JP | 04-065568 A | 3/1992 |
| JP | 07-138866 A | 5/1995 |
| RU | 2213548 | 3/1998 |
| WO | 93/15249 | 8/1993 |
| WO | WO 95/10995 A1 | 4/1995 |
| WO | 96/11107 | 4/1996 |
| WO | WO 96/14885 A1 | 5/1996 |

OTHER PUBLICATIONS

Molecular Weight Distributions, *Encyclopedia of Polymer Science and Engineering*, Second Edition, vol. 3, John Wiley & Sons, New York, 1985, pp. 299-300.

Coates, Geoffrey W. and Robert M. Waymouth, "Oscillating Stereocontrol: A Strategy for the Synthesis of Thermoplastic Elastomeric Polypropylene," *Science*, vol. 267, Jan. 13, 1995, pp. 217-219.

Cowie, J.M.G., "Solubility and the Cohesive Energy Density," *Polymers: Chemistry and Physics of Modern Materials*, Intext Educational Publishers, New York, 1973, pp. 142-145.

Lawrence, K.D. et al., "An Improved Device for the Formation of Superfine, Thermoplastic Fibers," *NRL Report 5265*, U.S. Naval Research Laboratory, Washington, D.C., Feb. 11, 1959.

Neumann, A.W., and R.J. Good, "Techniques of Measuring Contact Angles," Chapter 2, *Surface and Colloid Science—Experimental Methods*, vol. 11, edited by R.J. Good and R.R. Stromberg, pp. 31-91.

Wagener, K.B., "Oscillating Catalysts: A New Twist for Plastics," *Science*, vol. 267, Jan. 13, 1995, p. 191.

Wente, V.A. et al., "Manufacture of Superfine Organic Fibers," *NRL Report 4364*, U.S. Naval Research Laboratory, Washington, D.C., May 25, 1954, pp. 1-15.

Chinese Office Action regarding Chinese Application No. 200580021481.3 dated Aug. 7, 2009.

Israeli Office Action regarding Israeli Patent Application No. 178702 (Sep. 2, 2009).

Office action issued in related European Application No. 05760343.3, dated Aug. 10, 2010.

First Official Action for Russian Patent Application 2006146883 mailed Jan. 21, 2009.

* cited by examiner

ABSORBENT ARTICLE HAVING SHAPED ABSORBENT CORE FORMED ON A SUBSTRATE

FIELD OF THE INVENTION

This invention is directed to an absorbent article having an absorbent core which can be formed and shaped on a substrate during manufacture of the absorbent article.

BACKGROUND OF THE INVENTION

Personal care absorbent articles such as diapers, training pants, adult incontinence garments, absorbent swim wear, feminine hygiene articles and the like, typically include a liquid-permeable bodyside liner (sometimes called a "topsheet"), a liquid-impermeable outer cover (sometimes called a "backsheet"), and an absorbent core between the bodyside liner and the outer cover.

The absorbent core, which is typically formed separately from the other layers, receives and retains aqueous liquid such as urine, menses, etc. which are exuded by the wearer. Absorbent cores are commonly formed of superabsorbent particles or fibers, and hydrophilic absorbent fibers (e.g., cellulose), which are loosely mixed and entangled together to form an absorbent batt. Thermoplastic polymer fibers are sometimes also included to provide a reinforcing matrix. The processes for making conventional absorbent cores are relatively complex. The absorbent structures must be formed, bonded, shaped, and cut to form individual absorbent cores suitable for the particular absorbent articles. Accordingly, it has not been practical to integrate various processes for making absorbent cores with the processes employed to assemble the layer components of absorbent articles.

Full-width rectangular shaped absorbent cores can be formed in-line on a substrate and subsequently die cut or trimmed to a desired shape. This process results in substantial trim waste. If the waste cannot be recycled back into the manufacturing process, then the process becomes uneconomical. It would be desirable to produce the final shape of the absorbent core by in-line formation without requiring die cutting, thus avoiding these drawbacks.

During assembly of absorbent articles, it is known to secure the separately formed absorbent core to the bodyside liner, outer cover and/or intervening layer(s), using an adhesive, thermal bonding or ultrasonic bonding process. This securing is intended to prevent the absorbent core from shifting relative to the other layers during manufacture, storage, shipping and/or use of the absorbent article. If the layer to which the absorbent core is secured is stretchable or elastic, then securing the absorbent core in this manner may reduce the stretchability or elasticity of the layer. Alternatively, stretching of the outer cover, bodyside liner or other substrate layer can cause tearing of the absorbent core.

From a cost savings and performance standpoint, it would be advantageous to have an absorbent core which can be formed and shaped in-line during assembly of an absorbent article, and which does not prevent subsequent stretching (stretchability) of the layer(s) to which it is bound.

SUMMARY OF THE INVENTION

The present invention is directed to an absorbent article including at least a liquid-permeable bodyside liner, an outer cover, and an absorbent core between them. The absorbent core is formed and shaped in-line during assembly of the absorbent article, and is adhesively bound to the bodyside liner, the outer cover, and/or an intervening substrate layer, which can be stretchable. The absorbent core does not prevent stretching of the layer to which it is bound.

The absorbent core includes a combination of adhesive fibers and superabsorbent material. While the combination of adhesive fibers and superabsorbent material is bound to a substrate layer, the substrate layer is not considered to be part of the absorbent core. The absorbent core is "shaped," meaning that it is non-rectangular. The absorbent core has a central region, a front end region and a back end region. The absorbent core has an average width in the central region and a relatively wider average width in at least one of the end regions.

The absorbent core has an outer edge extending around its perimeter. Because the absorbent core is formed in-line, during assembly of the absorbent article as described herein, the outer edge of the absorbent core is uncut (i.e., devoid of cutting) along both lateral sides of the absorbent core. Due to the absence of cutting, the lateral sides of the absorbent core have an unevenness associated with tapering of the adhesive/superabsorbent combination. This unevenness may cause the lateral sides to have a fuzzy or serrated configuration of laterally extending peaks and valleys. The unevenness is characterized in that a Perimeter To Edge Length ratio ("P/EL") and a Mean Deviation From Mean Edge ("MDFME") for the absorbent core sides, as described herein, are both greater than for a die cut absorbent core having the same composition. The absorbent core suitably has a length equal to the length of the substrate, and a width which is narrower than the width of the substrate along the entire length of the absorbent core.

DEFINITIONS

Figure 1:
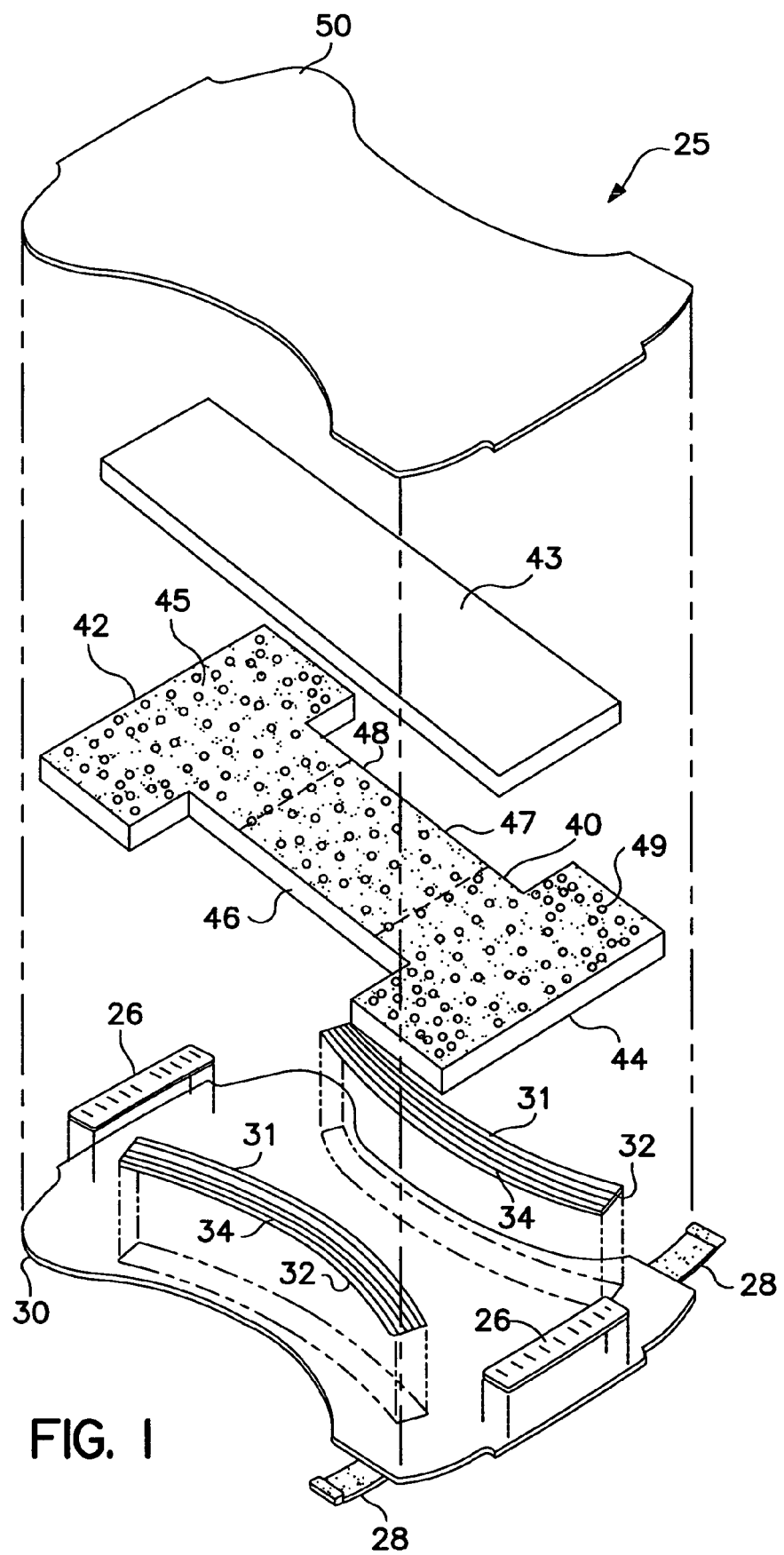
FIG. 1 is an exploded perspective view of an absorbent article according to the invention.

The term "absorbent material" refers to materials such as cellulose fibers which are capable of absorbing at least five times but generally less than 15 times their own weight of an aqueous solution containing 0.9% by weight sodium chloride. Absorbent material under the most favorable conditions can also include synthetic fiber matrices such as spunbond, meltblown and bonded carded webs, and the like. Also included are open structures such as through-air bonded carded webs, lofty through-air bonded bicomponent fiber spunbond webs, and other materials useful for rapid fluid intake.

The term "superabsorbent material" refers to water-swellable organic and inorganic materials that are capable of absorbing at least 15 times their own weight in a solution of 0.9% by weight aqueous sodium chloride under the most favorable conditions.

The term "personal care absorbent article" includes without limitation diapers, training pants, swim wear, absorbent underpants, adult incontinence garments, tissues, wet wipes, bed mats, and feminine hygiene articles.

The term "medical absorbent article" includes without limitation absorbent medical pads, drapes, wraps, bandages, and garments.

The term "attached" refers to the joining, adhering, connecting, bonding, or the like, of at least two elements. Two elements will be considered to be attached to one another when they are attached directly to one another or indirectly to one another, such as when each is directly attached to intermediate elements.

The term "cutting" refers to any method used to trim or cut the lateral side edges of an absorbent core, to form the absorbent core into a desired shape, typically a shape other than a pre-formed rectangle. Cutting processes include without limitation die cutting, water cutting, laser cutting, sawing and the like.

The term "generally perpendicular" means within about 15 degrees of perpendicular. Where "perpendicular" is defined by a 90-degree angle relative to a direction, "generally perpendicular" refers to an angle of about 75-105 degrees.

The term "hydrophilic" describes fibers or the surfaces of fibers and other materials which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, and fibers having contact angles greater than 90° are designated "non-wettable" or hydrophobic.

The term "layer" when used in the singular can have the dual meaning of a single element or a plurality of elements.

The term "liquid-impermeable," when used in describing a layer or multilayer laminate means that liquid body waste, such as urine, will not pass through the layer or laminate, under ordinary use conditions, in a direction generally perpendicular to the plane of the layer or laminate at the point of liquid contact.

The term "liquid-permeable" refers to any material that is not liquid impermeable.

The term "meltblown" refers to fibers formed by extruding a molten thermoplastic material through a plurality of fine, usually circular, die capillaries as molten threads or filaments into converging high velocity gas (e.g., air) streams, generally heated, which attenuate the filaments of molten thermoplastic material to reduce their diameters. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al.

Meltblowing processes can be used to make fibers of various dimensions, including macrofibers (with average diameters from about 40 to about 100 microns), textile-type fibers (with average diameters between about 10 and 40 microns), and microfibers (with average diameters less than about 10 microns). Meltblowing processes are particularly suited to making microfibers, including ultra-fine microfibers (with an average diameter of about 3 microns or less). A description of an exemplary process of making ultra-fine microfibers may be found in, for example, U.S. Pat. No. 5,213,881 to Timmons et al.

Meltblown fibers may be continuous or discontinuous and are generally self bonding when deposited onto a collecting surface. Meltblown fibers used in the present invention are suitably substantially continuous in length.

The term "nonwoven" as used in reference to a material, web or fabric refers to such a material, web or fabric having a structure of individual fibers or threads that are interlaid, but not in a regular or identifiable manner as in a knitted fabric. Nonwoven materials, fabrics or webs have been formed from many processes such as, for example, meltblowing processes, spunbonding processes, air laying processes, and bonded carded web processes. The basis weight of nonwovens is usually expressed in ounces of material per square yard (osy) or grams per square meter (gsm) and the fiber diameters are usually expressed in microns. (Note that to convert from osy to gsm, multiply osy by 33.91.)

The term "spunbond fibers" means small diameter fibers that are typically formed by extruding molten thermoplastic material as filaments from a plurality of fine usually circular capillaries of a spinneret with the diameter of the extruded filaments then being rapidly reduced as, for example, described in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Levy, and U.S. Pat. No. 3,542,615 to Dobo et al. Spunbond fibers are quenched and generally not tacky when they are deposited onto a collecting surface. Spunbond fibers are generally continuous and have average diameters frequently larger than 7 microns, more particularly, between about 10 and 20 microns.

The term "bonded carded webs" or "BCW" refers to nonwoven webs formed by carding processes as are known to those skilled in the art and further described, for example, in coassigned U.S. Pat. No. 4,488,928 to Alikhan and Schmidt which is incorporated herein in its entirety by reference. Briefly, carding processes involve starting with a blend of, for example, staple fibers with bonding fibers or other bonding components in a bulky batt that is combed or otherwise treated to provide a generally uniform basis weight. This web is heated or otherwise treated to activate the adhesive component resulting in an integrated, usually lofty nonwoven material.

The term "airlaying" or "airlaid" refers to a process by which a fibrous nonwoven layer can be formed. In the airlaying process, bundles of small fibers having typical lengths ranging from about 3 to about 19 millimeters (mm) are separated and entrained in an air supply and then deposited onto a forming screen, usually with the assistance of a vacuum supply. The randomly deposited fibers then are bonded to one another using, for example, hot air or a spray adhesive.

The terms "particle," "particles," "particulate," "particulates" and the like refer to superabsorbent material generally in the form of discrete units. The units can comprise granules, powders, spheres, pulverized materials or the like, as well as combinations thereof. The particles can have any desired shape such as, for example, cubic, rod-like, polyhedral, spherical or semi-spherical, rounded or semi-rounded, angular, irregular, etc. Shapes having a large greatest dimension/ smallest dimension ratio, like needles, flakes and fibers are also contemplated for inclusion herein. The terms "particle" or "particulate" may also include an agglomeration comprising more than one individual particle, particulate or the like. Additionally, a particle, particulate or any desired agglomeration thereof may be composed of more than one type of material. For instance, superabsorbent particles commonly include a core, shell, crosslinking agent, anti-dust treatment, etc., and may include one or more superabsorbent polymers.

The term "stretchable" refers to materials which, upon application of a stretching force, can be extended to a stretched dimension which is at least 150% of an original dimension (i.e., at least 50% greater than an original, unstretched dimension) in one or more directions without rupturing. The term "elastic" refers to materials which are stretchable and which, upon release of the stretching force, will retract (recover) by at least 50% of the difference between the stretched dimension and the original dimension. For instance, a material having an original dimension of 20 cm is stretchable if it can be extended to a dimension of at least 30 cm without rupture. The same material is elastic if, after being extended to 30 cm, it retracts to a dimension of 25 cm or less when the stretching force is removed. The conditions and test method by which the terms "stretchable" and "elastic" are defined are provided herein.

DETAILED DESCRIPTION OF THE PRESENTLY PREFERRED EMBODIMENTS

FIG. 1 illustrates a personal care absorbent article 25 according to the invention, in this case a disposable diaper. Disposable diaper 25 includes a liquid permeable bodyside liner 50, a surge material layer 43, an absorbent core 40, and an outer cover 30. The illustrated absorbent core 40 has an I-beam shape, and includes a front waist end 42, a rear waist end 44, and opposing lateral sides 46 and 48. For purposes of the invention, the absorbent core 40 is not limited to an I-beam shape, and may have an hour glass shape, or another suitable shape. In each case, the absorbent core 40 has a front end region 45, a central region 47 and a rear end region 49, each occupying about one-third of the longitudinal length of the absorbent core. The absorbent core has a first average width in the front end region 45, a second average width in the central region 47, and a third average width in the rear end region 49. At least one of the first and third average widths is wider than the second average width. The surge layer and other layers can also have different shapes and dimensions.

The surge layer 43 and bodyside liner 50 are constructed from highly liquid pervious (generally non-absorbent) materials. These layers transfer liquid from the wearer to the absorbent core. Suitable liquid pervious materials include porous woven materials, porous nonwoven materials, films with apertures, open-celled foams, and batting. Examples include, without limitation, any flexible porous sheets of polyolefin fibers, such as polypropylene, polyethylene or polyester fibers; webs of spunbonded polypropylene, polyethylene or polyester fibers; webs of rayon fibers; bonded carded webs of synthetic or natural fibers or combinations thereof. U.S. Pat. No. 5,904,675, issued 18 May 1999 to Laux et al., provides further examples of suitable surge materials. The bodyside liner and surge layer can be composed of substantially hydrophobic materials, and can be treated with a surfactant or otherwise processed to impart a desired level of wettability and hydrophilicity.

The bodyside liner 50 typically overlies the absorbent core 40 and surge layer 43, and may not have the same dimensions as outer cover 30. The bodyside liner is desirably compliant, soft feeling and non-irritating to the wearer's skin. The bodyside liner and surge layer may be less hydrophilic than the absorbent core, to present a dry surface to the wearer and facilitate penetration of liquid to the absorbent core. The bodyside liner and surge layer can be composed of substantially hydrophobic materials, and can be treated with a surfactant or otherwise processed to impart a desired level of hydrophilicity.

In a particularly suitable embodiment, the bodyside liner 50 is stretchable or elastic. For example, in one embodiment, the bodyside liner 50 can be a nonwoven, spunbond polypropylene fabric which has been neck-stretched to approximately 40% of its original width. Strands of KRATON® G2760 elastomer material may be adhered to the necked spunbond material. The fabric can be surface treated with an operative amount of surfactant, such as about 0.45% AHCOVEL® Base N62 surfactant, available from Uniqema, a division of ICI, a business having offices located in New Castle, Del. The surfactant can be applied by any conventional means, such as spraying, printing, brush coating or the like.

In other embodiments, the stretchable bodyside liner 50 can include elastic strands or netting, LYCRA® elastics, cast or blown elastic films, nonwoven elastic webs, meltblown or spunbond elastomeric fibrous webs, as well as combinations thereof. Examples of suitable elastomeric materials include KRATON® elastomers, HYTREL® elastomers, ESTANE® elastomeric polyurethanes (available from B.F. Goodrich and Company located in Cleveland, Ohio), PEBAX® elastomers, and elastomeric polyolefins such as VISTAMAXX™ (available from Exxon Mobil Corporation of Irving, Tex.), AFFINITY® (available from Dow Chemical of Midland, Mich.), and the like. The bodyside liner 50 may include blends or laminates of fibers, scrim, webs, necked webs and films with perforations, apertures, creping, heat activation, embossing, micro-straining, chemical treatment, or the like, as well as combinations thereof including homofilaments, bicomponent filaments of the sheath/core or side-by-side configuration, or biconstituent filaments comprising blends of polymers, wherein the composite filaments exhibit stretchable or elastic properties.

The outer cover 30 is generally substantially liquid impermeable to inhibit body exudates against leaking from the absorbent article 25 and wetting articles, such as bed sheets and clothing, as well as the wearer and caregiver. The outer cover 30 may be constructed of a single layer of liquid impermeable material or more suitably it may be a multi-layered laminate structure in which at least one of the layers is liquid impermeable. For instance, the outer cover 30 can include a liquid permeable outer layer and a liquid impermeable inner layer joined together by a laminate adhesive, or by ultrasonic bonds, thermal bonds, or the like. In such an embodiment, the inner layer of the outer cover 30 can be both liquid and vapor impermeable, or it may be liquid impermeable and vapor permeable. For example, the inner layer can be manufactured from a thin plastic film, although other flexible liquid impermeable materials may be used.

Alternative constructions of the outer cover 30 may comprise a woven or nonwoven fibrous web layer which has been totally or partially constructed or treated to impart the desired levels of liquid impermeability to selected regions that are adjacent or proximate the absorbent composite. For example, the outer cover may include a gas-permeable, nonwoven fabric layer laminated to a polymer film layer which may or may not be gas-permeable. Other examples of fibrous, cloth-like outer cover materials can comprise a stretch thinned or stretch thermal laminate material.

In a particularly suitable embodiment, the outer cover 30 is stretchable, and even more suitably the outer cover is elastic. As an example, outer cover 30 may be composed of a single layer, multiple layers, laminates, spunbond fabrics, films, meltblown fabrics, elastic netting, microporous web, bonded carded webs or foams comprised of elastomeric or polymeric materials. Elastomeric nonwoven laminate webs may include a nonwoven material joined to one or more gatherable nonwoven webs, films, or foams. Stretch bonded laminates (SBL) and neck bonded laminates (NBL) are examples of elastomeric composites. Examples of suitable nonwoven materials are spunbond-meltblown fabrics, spunbond-meltblown-spunbond fabrics, spunbond fabrics, or laminates of such fabrics with films, foams, or other nonwoven webs.

Suitable elastomeric materials may include cast or blown films, foams, or meltblown fabrics composed of elastomeric polyethylene, polypropylene, or polyolefin copolymers, as well as combinations thereof. The elastomeric materials may include PEBAX® elastomer (available from AtoChem located in Philadelphia, Pa.), HYTREL® elastomeric polyester (available from E. I. DuPont de Nemours located in Wilmington, Del.), KRATON® elastomer (available from Kraton Polymers of Houston, Tex.), or strands of LYCRA® elastomer (available from E. I. DuPont de Nemours located in Wilmington, Del.), or the like, as well as combinations thereof. The outer cover 30 may include materials that have elastomeric properties through a mechanical process, a printing process, a heating process, and/or a chemical treatment. For examples such materials may be apertured, creped, neck-stretched, heat activated, embossed, and micro-strained.

Attached to outer cover 30 are waist elastics 26, leg elastics 31, and fastening tabs 28, which may be of any conventional structure. Waist elastics 26 may include without limitation a plurality of elastic strands joined to a carrier sheet and placed between two spunbond webs. Leg elastics 31 may include a carrier sheet 32 and individual elastic strands 34. Fastening tabs 28 may include fastening tapes or mechanical fasteners such as VELCRO hook and loop fastening elements. The waist elastics 26 and leg elastics 31 may be joined to the outer cover 30 or, alternatively, the bodyside liner 50, or both, along the respective leg openings and waist edges of the absorbent article 25.

The bodyside liner 50 and outer cover 30 are suitably attached to one another, for example, by being directly attached to each other such as by affixing the outer cover 30 directly to the liner 50, or by being indirectly attached to each other such as by affixing the bodyside liner to intermediate components of the absorbent article 25 which in turn are affixed to the outer cover. The bodyside liner 50 and the outer cover 30 can, for example, be attached to each other along at least a portion of their periphery by adhesive, by ultrasonic bonding, by thermal bonding or by other suitable attachment techniques known in the art.

Figure 2:
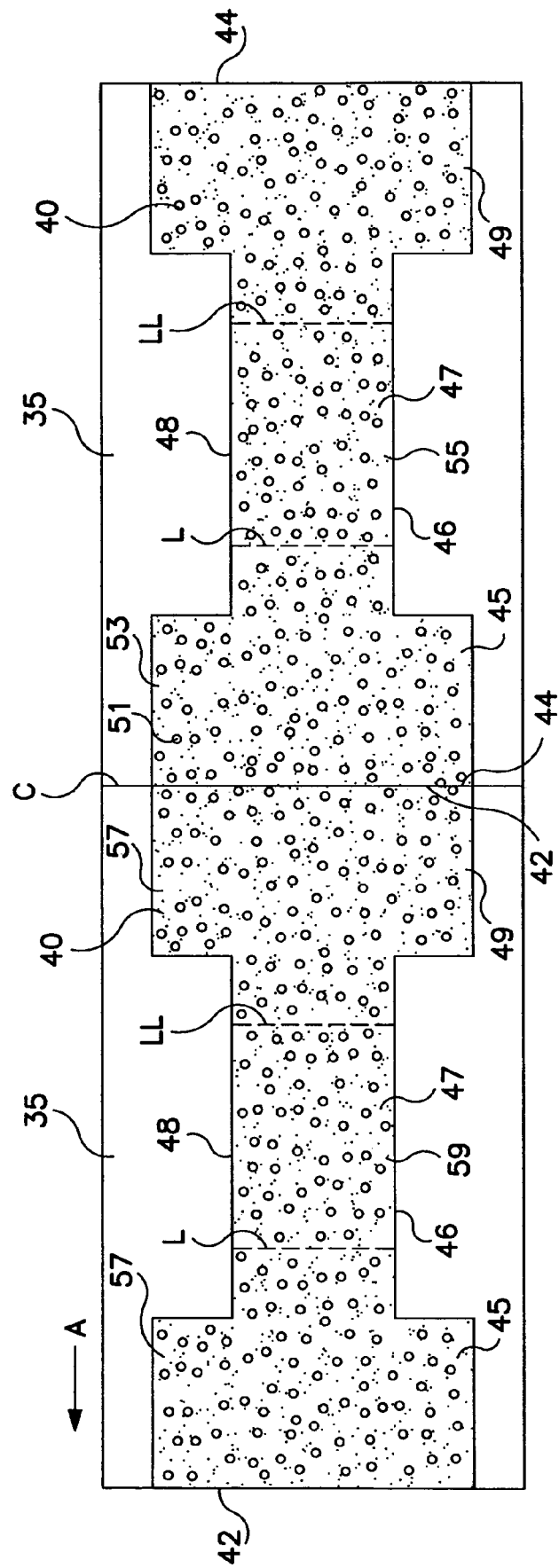
FIG. 2 is a plan view of adjacent absorbent cores formed on a substrate according to the invention.

In the embodiment shown in FIG. 1, the absorbent core may be formed using any of the adjacent layers (e.g., bodyside liner 30 and/or surge layer 43) as a substrate. Alternatively, the absorbent core 40 may be formed on an intervening substrate layer (not shown in FIG. 1), such as a spacer layer between the absorbent core 40 and outer cover 30, or another substrate layer. FIG. 2 illustrates a continuous substrate layer 35 on which a plurality of absorbent cores 40 may be continuously formed end-to-end as the substrate 35 travels in a direction indicated by arrow "A". The front end region 45 of each absorbent core transitions into a central region 47 along imaginary line "L." The central region 47 of each absorbent core transitions into a rear end region 49 along imaginary line "LL." Initially, prior to separation, the front end 42 of each absorbent core is joined to the rear end 44 of the immediately preceding absorbent core along an imaginary cutting line "C" representing the location of a subsequent cut following the formation of each absorbent core 40.

The absorbent core 40 includes a combination of superabsorbent particles 51 and adhesive fibers 53 formed by deposition onto the substrate layer 35. By action of the adhesive, the absorbent core is attached to the substrate along an entire upper or lower surface of the absorbent core. The superabsorbent particles 51 and adhesive fibers 53 may be applied separately or together. For instance, the adhesive fibers 53 may first be applied to the substrate layer 35 in a pattern representing the shape of the absorbent cores 40. Then, the superabsorbent particles 51 may be applied directly over the adhesive fibers 53. Alternatively, the superabsorbent particles 51 may be pre-combined with the adhesive material, and the combination may be applied to the substrate layer 35 in a pattern representing the shape of absorbent cores 40. Alternatively, the adhesive fibers 53 and superabsorbent particles 51 may be applied in multiple, alternating layers. In any case, the absorbent core 40 may include about 40-99% by weight superabsorbent particles and about 1-60% by weight adhesive, suitably about 80-98% by weight superabsorbent particles and about 2-20% by weight adhesive, particularly about 85-95% by weight superabsorbent particles and about 5-15% by weight adhesive. The absorbent core 40 may also include cellulose fibers and other ingredients.

The superabsorbent particles 51 in absorbent core 40 may be particles of any superabsorbent material which meets the absorbency requirement indicated above. Specifically, the superabsorbent material is a water-swellable, water-insoluble material that absorbs at least about 15 times its weight, suitably at least about 25 times its weight of an aqueous solution containing 0.9% by weight sodium chloride, under the most favorable conditions. The superabsorbent material can be selected from natural, synthetic, and modified natural polymers. The superabsorbent material can include inorganic materials, such as silica gels, or organic compounds, such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or VanderWaals forces. Examples of suitable synthetic superabsorbent material polymers include alkali metal and ammonium salts of poly(acrylic acid) and poly(methacrylic acid), poly(acrylamides), poly (vinyl ethers), hydrolized maleic anhydride copolymers with vinyl ethers and alpha-olefins, poly(vinyl pyrrolidone), poly (vinylmorpholinone), poly(vinyl alcohol), or basic or chloride and hydroxide salts of polyvinyl amine, polyamine polyquarternary ammonium, polyamine, hydrolyzed polyamide, and mixtures and copolymers thereof. These superabsorbent materials are at least partially crosslinked.

Other suitable superabsorbent material polymers include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Additional suitable superabsorbent materials are disclosed in U.S. Pat. No. 3,901, 236 issued Aug. 26, 1975 and processes for preparing synthetic absorbent gelling polymers are disclosed in U.S. Pat. No. 4,076,663 issued Feb. 28, 1978 and U.S. Pat. No. 4,286,082 issued Aug. 25, 1981.

Suitable superabsorbent materials are commercially available from various suppliers. For example, SXM 9543 and FAVOR 880 are suitable superabsorbent materials available from Stockhausen, Inc. of Greensboro, N.C., U.S.A., and DRYTECH 2035 is a suitable superabsorbent material available from Dow Chemical Company of Midland, Mich., U.S.A. Another suitable superabsorbent material is a multicomponent superabsorbent particulate gel from BASF of Ludwigshafen, Germany designated E1231-99. Multicomponent superabsorbent gel particles and methods to prepare them are described in U.S. Pat. Nos. 5,981,689; 6,072,101; 6,087,448; 6,121,409; 6,159,591; 6,194,631; 6,222,091; 6,235,965; 6,342,298; 6,376,072; 6,392,116; 6,509,512; and 6,555,502; U.S. Patent Publications 2001/01312; 2001/07064; 2001/29358; 2001/44612; 2002/07166; 2002/15846; and 2003/14027; and PCT Publications WO 99/25393; WO 99/25745; WO 99/25748; WO 00/56959; WO 00/63295; WO 02/10032; WO 03/18671; and WO 03/37392; the disclosures of which are incorporated by reference to the extent they are consistent herewith. Superabsorbent materials may also be formed by in situ polymerization on a substrate.

The superabsorbent material particles 51 used in forming the absorbent core 40 can be of any desired configuration, such as spiral or semi-spiral, cubic, rod-like, polyhedral, random, spherical (e.g., beads), needles, flakes, fibers, porous particles and foam particles. Conglomerates of particles of superabsorbent material may also be used in forming the absorbent core 40. As an example, in a particularly suitable embodiment the superabsorbent material particles have an average dry particle size in the range of from about 20 micrometers to about 1 millimeter. "Dry particle size" as used herein means the weighted average of the smallest dimension of the individual particles when they are in the dry state.

In one embodiment, the adhesive fibers 53 are formed of a hot melt adhesive. Such an adhesive generally includes one or more polymers to provide cohesive strength (e.g., aliphatic polyolefins such as ethylene-propylene copolymers, polyetheramides, polyetheresters, and combinations thereof; ethylene vinyl acetate copolymers; styrene-butadiene or styrene-isoprene block copolymers; etc.); a resin or analogous material (sometimes called a tackifier) to provide adhesive strength (e.g., hydrocarbons distilled from petroleum distillates; rosins and/or rosin esters; terpenes derived, for example, from wood or citrus, etc.); optional waxes, plasticizers or other materials to modify viscosity (e.g., mineral oil, polybutene, paraffin oils, ester oils, and the like); and/or other additives including, but not limited to, antioxidants or other stabilizers.

As an example, the hot melt adhesive may contain from about 15 to about 50 weight percent cohesive strength polymer or polymers, from about 30 to about 65 weight percent resin or other tackifier or tackifiers, from more than zero to about 30 weight percent plasticizer or other viscosity modifier, and optionally less than about 1 weight percent stabilizer or other additive. Other hot melt adhesive formulations including different weight percentages of these components are possible. The adhesive may either be hydrophilic or hydrophobic without departing from the scope of this invention.

In a particularly suitable embodiment, the adhesive has a viscosity of less than about 10,000 centipoises (cps) at a temperature of less than or equal to about 400° F. (204° C.), more suitably at a temperature of less than or equal to about 300° F. (149° C.), and still more suitably at a temperature of less than or equal to about 250° F. (121° C.). In another embodiment, the adhesive has a viscosity in the range of about 1,000 cps to about 8,000 cps at a temperature of about 300° F. (149° C.), and still more suitably in the range of about 2,000 cps to about 6,000 cps at a temperature of about 300° F. (149° C.).

As used herein, the "viscosity" of the adhesive is defined as the viscosity determined using the Viscosity Test set forth later herein. Using a relatively low viscosity adhesive promotes sufficient contact with (e.g., coating of) the particulate superabsorbent material, thereby more readily capturing and holding the superabsorbent material particles.

Low viscosity adhesives can be processed, i.e., melted and applied to the substrate layer 35 or other layer components of the absorbent article 25 as will be described later herein, at lower processing temperatures, thereby promoting ease of manufacturing. A lower processing temperature also reduces the risk of thermal degradation of the substrate (e.g., the outer cover 30 or other substrate layer 35) on which the absorbent core 40 is formed. As an example, the adhesive is suitably processable at temperatures in the range of about 200° F. (93° C.) to about 400° F. (204° C.), and more suitably in the range of about 250 to about 360° F. (about 121 to about 182° C.). The adhesive has a viscosity less than about 10,000 centipoise; suitably about 1,000-8,000 centipoise, particularly about 2,000-6,000 centipoise at the processing temperature.

The adhesive also has a suitably low storage modulus (G'). The storage modulus of the adhesive generally refers to the ability of the adhesive (after it has set up or otherwise generally dried, e.g., after cooling) to deform, such as upon flexing of the outer cover 30 or other substrate 35 on which the absorbent core 40 is formed, without a substantial loss of integrity of the adhesive. By using an adhesive having a relatively low storage modulus, the absorbent core 40 formed on the substrate is suitably generally soft and flexible to permit flexing of the absorbent core 40 along with the substrate. More specifically, the storage modulus is a coefficient of elasticity representing the ratio of stress to strain as the adhesive is deformed under a dynamic load.

As used herein, the storage modulus of the adhesive is reported as measured according to the Rheology Test set forth in detail later herein. As an example, the storage modulus (G') of the adhesive as determined by the Rheology Test is suitably less than or equal to about $1.0 \times 10^7$ dyne/cm$^2$ at 25° C., is more suitably in the range of about $1.0 \times 10^4$ to about $1.0 \times 10^7$ dyne/cm$^2$ at 25° C., and is still more suitably in the range of about $1.0 \times 10^5$ to about $1.0 \times 10^6$ dyne/cm$^2$ at 25° C.

The adhesive also suitably has a glass transition temperature (Tg) in the range of about −25 to about 25° C., and more suitably in the range of about −10 to about 25° C. The "glass transition temperature" as used herein refers generally to the molecular mobility of the adhesive. For example, where the temperature of the adhesive is below the glass transition temperature (Tg), it tends to be more rigid and brittle, and where the temperature of the adhesive is above the glass transition temperature (Tg) the adhesive has more of a tendency to flow. However, in the event that the adhesive temperature substantially exceeds its glass transition temperature (Tg), the adhesive can have substantially reduced adhesive properties. Thus, the glass transition temperature of the adhesive is suitably close to the temperature at which the adhesive is to be used (e.g., room temperature). The glass transition temperature (Tg) of the adhesive as used herein refers to the glass transition temperature as measured by the Rheology Test set forth later herein.

Some examples of suitable adhesives for use in forming the absorbent composite 44 are hot-melt adhesives commercially available from National Starch and Chemical Co. of Bridgewater, N.J., under the designations 34-5610 and 34-447A. Other examples of suitable adhesives are those made by Bostik-Findley in Milwaukee, Wis. under the designations HX 4207-01, HX 2773-01, H2525A and H2800. Other suitable adhesives may alternatively, or additionally, be used without departing from the scope of this invention. Moreover, the term "adhesive" as used herein is not intended to exclude materials, substances, compositions and the like designated by a term other than "adhesive" or "adhesive composition" but having the characteristics of and functioning in accordance with the adhesives described herein.

Referring again to FIG. 2, the absorbent core 40 (including superabsorbent particles 51 and adhesive fibers 53) may be formed on the substrate layer 35 (or other substrate) at a basis weight of about 20-1500 grams per square meter (gsm), suitably about 50-1000 gsm, particularly about 100-750 gsm. The adhesive component of absorbent core 40 may have a basis weight of about 1-100 gsm, suitably about 4-75 gsm. The remaining basis weight of absorbent core 40 may be composed of superabsorbent particles. The superabsorbent particles in absorbent core 40 may have a basis weight of about 10-1400 gsm, suitably about 40-1000 gsm. Depending on the bulk density of the absorbent core 40 and its basis weight, the absorbent core 40 may have a thickness ranging from less than one millimeter to several millimeters.

Because the absorbent core 40 is formed and shaped on the substrate layer 35, or other substrate, the absorbent core 40 has lateral sides 46 and 48 which have not been cut, and which have numerous lateral projections 55 causing the lateral sides to have a fuzzy appearance. Each fuzzy edge is characterized by a Perimeter/Edge Length ratio (P/EL) which is greater than for an absorbent core of identical composition having a die cut edge. Typically, the P/EL for the lateral sides 46 and 48 is greater than or equal to 1.25, and is suitably greater than or equal to 1.50, or 2.0, or 4.0, or 6.0, or 8.0, or 10.0, or 12.0, or 14.0. Each fuzzy edge is further characterized by a Mean Deviation From Mean Edge (MDFME) which is greater than for an absorbent core of identical composition having a die cut edge. Typically, the MDFME for the lateral sides 46 and 48 is greater than or equal to 0.7 mm, and is suitably greater than or equal to 1.0 mm or 1.5 mm, or 2.0 mm.

The absorbent core 40 is both formed and shaped on the substrate layer 35 or other substrate. The term "shaped" means that at least one end region 45 or 49 of the absorbent core 40 has an average width (in the lateral direction) which is greater than the average width in the central region 47. The average width in the at least one end region may be at least about 5% greater, suitably at least about 10% greater, particularly at least about 25% greater, or at least about 50% greater than the average width in the central region 47. In one embodiment of absorbent core 40, both end regions (45 and 49) have an average width which is greater, or at least about 5% greater, or at least about 10% greater, or at least about 25% greater, or at least about 50% greater than the average width of central region 47. The absorbent core 40 may have an I-beam shape as illustrated, a "T" shape, an hourglass shape, a dumbbell shape, a mushroom shape, or any suitable shape.

As illustrated in FIG. 2, the absorbent cores 40 can be formed end-to-end on substrate layer 35 and are then separated by cutting both the absorbent core material and the substrate material along a cutting line "C." The resulting absorbent core 40 has a length equal to the length of substrate 35, and a width narrower than the width of substrate 35 along the entire length of the absorbent core 40. Alternatively, absorbent cores 40 can be formed with spaces between them.

As explained above, the substrate to which the absorbent core 40 is applied may be an outer cover, bodyside liner, surge layer, or another intervening layer. Collectively, the substrate may be a film, apertured film, fibrous web, foam layer, or a combination of the foregoing materials. Fibrous nonwoven webs, and combinations including a fibrous nonwoven web, are particularly suitable. Fibrous nonwoven webs include without limitation spunbond webs, meltblown webs, spunbond-meltblown-spunbond (SMS) web laminates, spunbond-meltblown (SM) web laminates, bonded carded webs, hydraulically entangled webs, air laid webs, and the like. The fibrous nonwoven web substrate may have a basis weight of about 5-100 gsm, suitably about 10-50 gsm.

The substrate layer is suitably stretchable, and is particularly suitably elastic. Stretchable substrate layers may, upon application of a stretching force, be capable of extending to a stretched dimension (in at least one direction) which is at least 150% of an original dimension, suitably at least 200% of an original dimension, particularly at least 250% of an original dimension, without rupture. Elastic substrate layers are stretchable and will, upon release of the stretching force, retract by at least 50% of the difference between the stretched length and the original (unstretched) length, suitably by at least 75% of the difference, or by substantially all of the difference. Stretchable and/or elastic substrate layers may exhibit these properties in only one direction, in more than one direction, or in every direction.

Stretchable and elastic substrate layers may be formed of a stretchable or elastic polymer, including without limitation, elastomeric polyolefins (e.g., single-site catalyzed olefin copolymers), polyether amides (e.g., the PEBAX® elastomers identified above), polyether esters (e.g., the HYTREL® elastomers identified above), styrene-olefin block copolymer elastomers (e.g., the KRATON® elastomers identified above), and combinations including a stretchable or elastic polymer. Stretchable and elastic substrate layers may also be formed of materials that are rendered elastic via mechanical processing, including without limitation neck-stretched fibrous nonwoven webs, neck-bonded laminates including a neck-stretched fibrous nonwoven web and a stretchable or elastic layer, crimped nonwoven webs, creped nonwoven webs, selectively mechanically prestrained nonwoven webs and films, and selectively apertured nonwoven webs and films.

Figure 3:
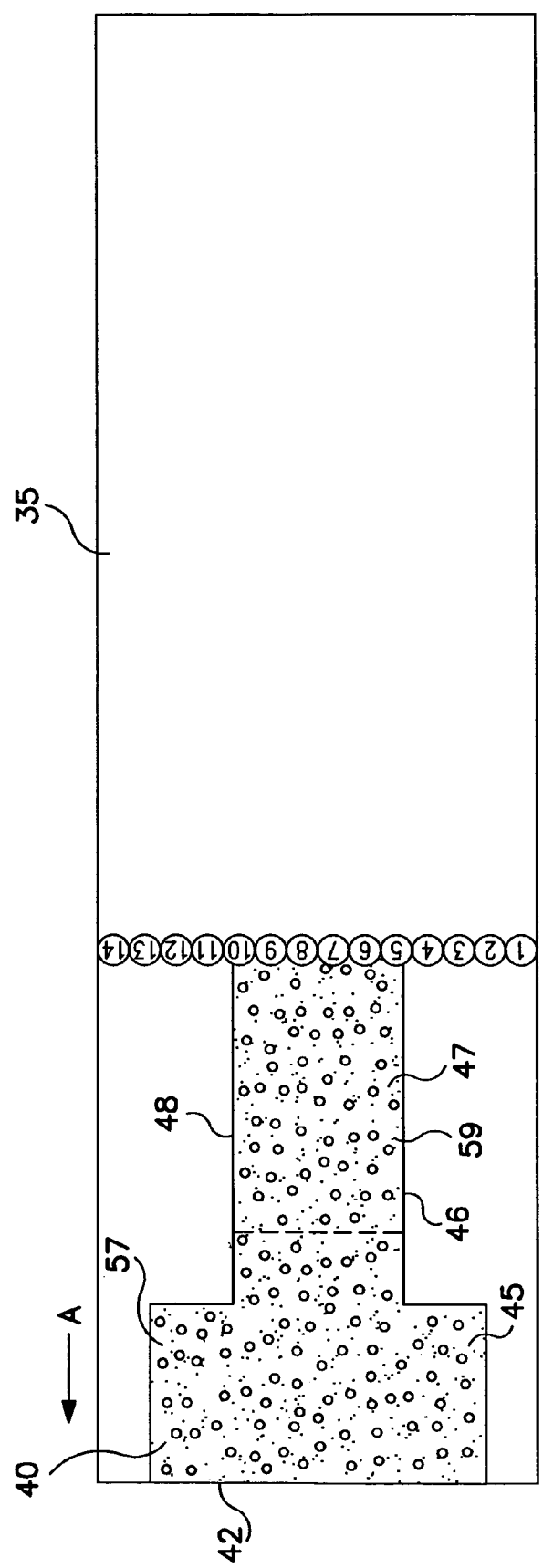
FIG. 3 schematically illustrates a process for forming and shaping the adhesive component of the absorbent core on a substrate.

FIG. 3 schematically illustrates a melt blowing process useful for applying the adhesive component of the absorbent core 40 illustrated in FIG. 2. Fourteen meltblowing nozzles, numbered sequentially 1 through 14, are positioned above the substrate 35 and across its width as the substrate 35 travels in the direction of the arrow "A." Each of the fourteen nozzles can be individually programmed to be constantly "on," constantly "off," or "on" and "off" for alternating periods. Adhesive will be applied to substrate layer 35 from a particular nozzle only when that nozzle is turned "on." Once the programming has been completed for a particular configuration of absorbent core 40, the individual nozzles will be automatically turned "on" and/or "off," as desired, and will be synchronized with the movement of substrate layer 35.

To make the absorbent core 40 illustrated in FIGS. 2 and 3, the end nozzles 1 and 14 will be constantly "off." The six middle nozzles 5, 6, 7, 8, 9 and 10 will be constantly "on." The remaining nozzles 2, 3, 4, 11, 12 and 13 will be "on" about 50% of the time and "off" about 50% of the time. The reason is that each of the end regions 45 and 49 of absorbent core 40 includes a widened portion 57 which extends about 25% of the length of the absorbent core. Each absorbent core 40 also includes a narrower portion 59 extending about 50% of its length. Because the absorbent cores are manufactured in sequence, end-to-end as shown in FIG. 2, the continuous manufacture of absorbent cores 40 requires nozzles 2, 3, 4, 11, 12 and 13 to be "on" 50% of the time, then "off" 50% of the time, in alternating periods. If absorbent cores 40 are manufactured with spaces between them, then all of the nozzles 1-14 may have brief "off" periods to allow for the spaces.

By way of example, if the substrate layer 35 is traveling at a line speed of 200 meters/min. and each absorbent core 40 has a length of 40 centimeters, then 0.12 seconds will be required for the nozzles 1-14 to span a single absorbent core length. The nozzles 2, 3, 4, 11, 12 and 13 will thus be "on" and "off" for alternating periods of 0.06 seconds each. If the widened regions 57 collectively cover only one-third of the length of absorbent core 40 (instead of 50% as illustrated in the drawings), then the nozzles 2, 3, 4, 11, 12 and 13 will be "on" and "off" for alternating periods of 0.04 seconds "on" and 0.08 seconds "off."

The widened regions 57 can be made wider by programming the end nozzles 1 and 14 to switch "on" and "off" for alternating periods of time. The widened regions 57 can be made narrower by maintaining nozzles 1, 2, 13 and 14 in a constant "off" position. The widened regions 57 can be made longer or shorter by varying the relative durations of the alternating "on" and "off" periods. The widened regions 57 can be formed into different shapes (e.g., triangular, trapezoidal, parabolic or semi-circular) by varying the durations of the "on" periods and "off" periods for different nozzles. For instance, nozzles 4 and 11 may have a longer "on" period and shorter "off" period than nozzles 3 and 12, which in turn may have a longer "on" period and shorter "off" period than nozzles 2 and 13.

The number and size of the meltblown nozzles may also be varied. The nozzles need not be arranged in a straight line as shown in FIG. 3, but may instead be staggered relative to each other. The nozzles may also be programmed to deliver different flow rates of adhesive (relative to other nozzles) so that the absorbent core 40 may have a shaped profile in the "Z" direction (perpendicular to the drawing) as well as in the "X" and "Y" directions (in the plane of the drawing). The "on" and "off" periods of nozzles 2, 3, 4, 11, 12 and 13, and/or the cutting of absorbent cores 40 from the continuous moving web illustrated in FIGS. 2 and 3, may be timed to produce widened regions 57 in either one or both end regions 45 and 49 of the absorbent core 40. The nozzles 1-14 may also be programmed to provide the central region 47 (and the narrower region 59) of the absorbent core 40 with a curved or otherwise shaped (e.g., convex) configuration. More than one row of adhesive deposition nozzles may also be present, as described with reference to FIG. 5. The superabsorbent particles 51 may be combined and applied together with adhesive fibers 53, or may be applied as one or more separate layers, as discussed with reference to FIGS. 5 and 6.

Figure 4:
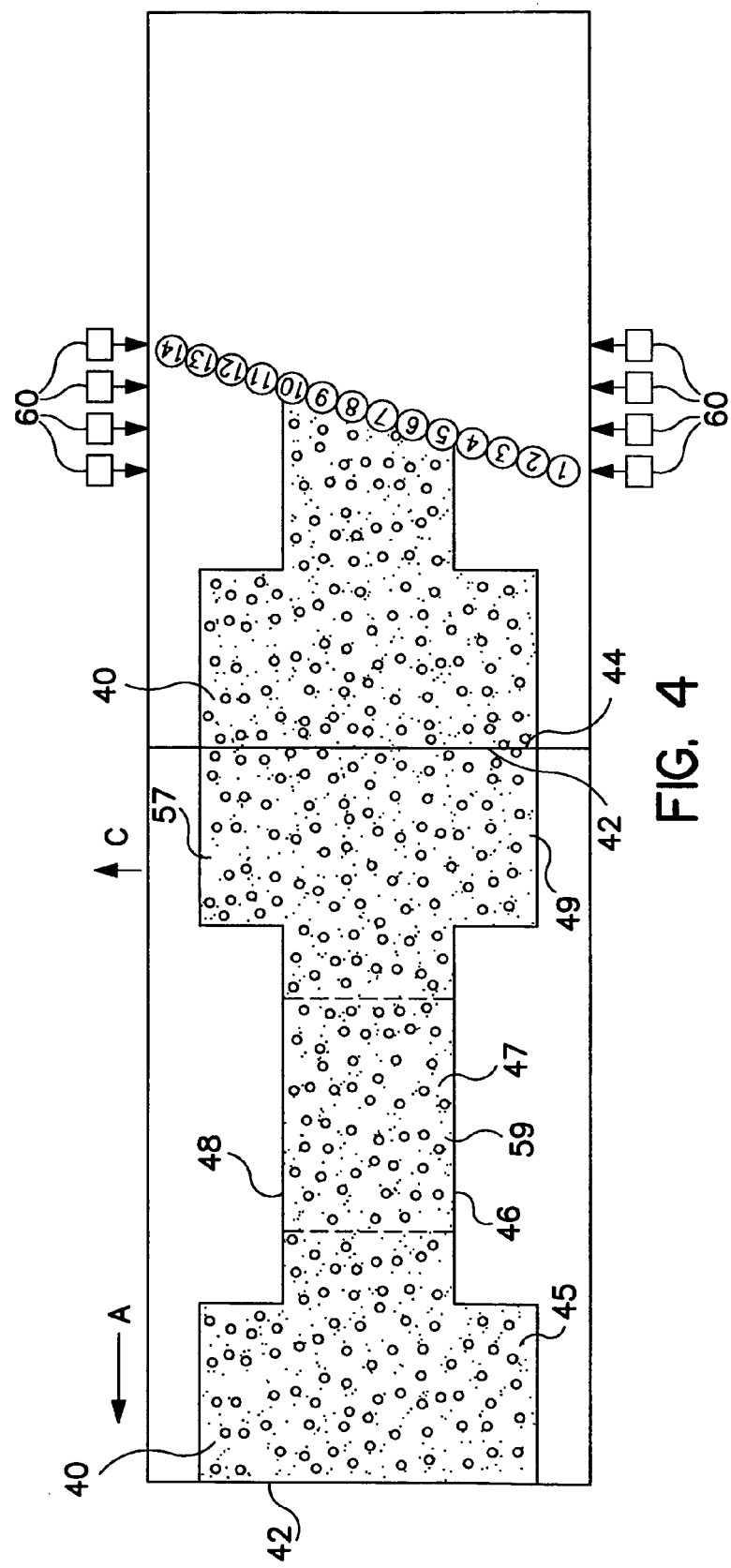
FIG. 4 schematically illustrates an alternative process for forming and shaping the adhesive component of the absorbent core on a substrate.

FIG. 4 schematically illustrates an alternative process for applying the adhesive fibers 53, with or without superabsorbent particles 51, to the continuously moving substrate 35. In the illustrated process, the adhesive spray nozzles 1-14 may be staggered at an angle from the cross direction "C" of substrate 35, and are no longer perpendicular to the machine direction (which is the direction of arrow "A"). The alignment of spray nozzles 1-14 may vary between 0-80 degrees in either direction from the cross direction "C," suitably between about 5-60 degrees in either direction from the cross direction "C."

In the process of FIG. 4, the nozzles 1-14 may each supply a continuous stream of adhesive, and be continuously "on." Alternatively, some of the nozzles (e.g., nozzles 2-13) may be continuously "on" with the remaining nozzles (e.g., nozzles 1 and 14) being continuously "off." Instead of using intermittent adhesive pulses to shape the absorbent core 40, the shaping is provided by one or more air nozzles "60" on both sides of the substrate 35.

The air nozzles 60 deliver air jets at predetermined velocities, sufficient to urge the continuous adhesive streams from at least the outer adhesive nozzles (e.g., nozzles 1-4 and 11-14) inward and toward the center of the substrate 35 at periodic intervals. The periodic intervals of air may be effected by periodically switching the air nozzles 60 "on" and "off," or by periodically blocking the air nozzles 60 so that they do not manipulate the adhesive streams, or manipulate the adhesive streams to a lesser extent, at periodic intervals. One or more air nozzles 60 may be positioned on both lateral sides of the substrate 35 and directed toward the adhesive streams emanating from adhesive nozzles 1-14. The air nozzles 60 may have an opening diameter of about 0.5-5 mm, suitably about 1-3 mm, depending on the size of absorbent core 40, line speed, number of air nozzles, air pressure, adhesive basis weight, and other process variables.

Referring to the above example in which the substrate layer 35 travels at 200 meters/min., each absorbent core 40 has a length of 40 cm, and the widened regions 57 of absorbent core 40 collectively encompass 50% of its length, a period of 0.12 seconds would be required for the adhesive nozzles 1-14 to span a single absorbent core length. The air nozzles 60 would thus be "on" (and not blocked) for 0.06 seconds, followed by "off" (or blocked) for 0.06 seconds, in alternating periods. If the widened regions 57 instead collectively covered one-third of the length of absorbent core 40, then the air nozzles 60 would be "on" (and not blocked) followed by "off" (or blocked) for alternating periods of 0.04 seconds and 0.08 seconds, respectively.

One consequence of using air jets to shape the absorbent core 40, instead of varying the amount of adhesive and superabsorbent, is that the narrower region 59 of the resulting absorbent core 40 has a higher basis weight than the one or two wider regions 57. This is because the amount of adhesive and superabsorbent is not varied along the length of absorbent core 40, but is instead redistributed to wider and narrower regions.

The use of staggered nozzles 1-14 is not limited to the process of FIG. 4, and can also be employed with the process described with respect to FIG. 3. When employed with respect to FIG. 3, the staggering of nozzles 1-14 will impact the precise timing of when the intermediate nozzles (e.g., nozzles 2-4 and 11-13) are switched "on" and "off," with the upstream nozzles being turned "on" sooner and "off" sooner than the downstream nozzles. The lengths of the periods during which these nozzles are "on" and "off" will not be affected by the staggering.

Similarly, the use of air jets as described with respect to FIG. 4 may also be practiced with adhesive nozzles 1-14 aligned perpendicular to the machine direction, as shown in FIG. 3. Precise control of the adhesive deposition may be more difficult because the air jets will urge several of the adhesive streams together before they contact the substrate 35.

Figure 5:
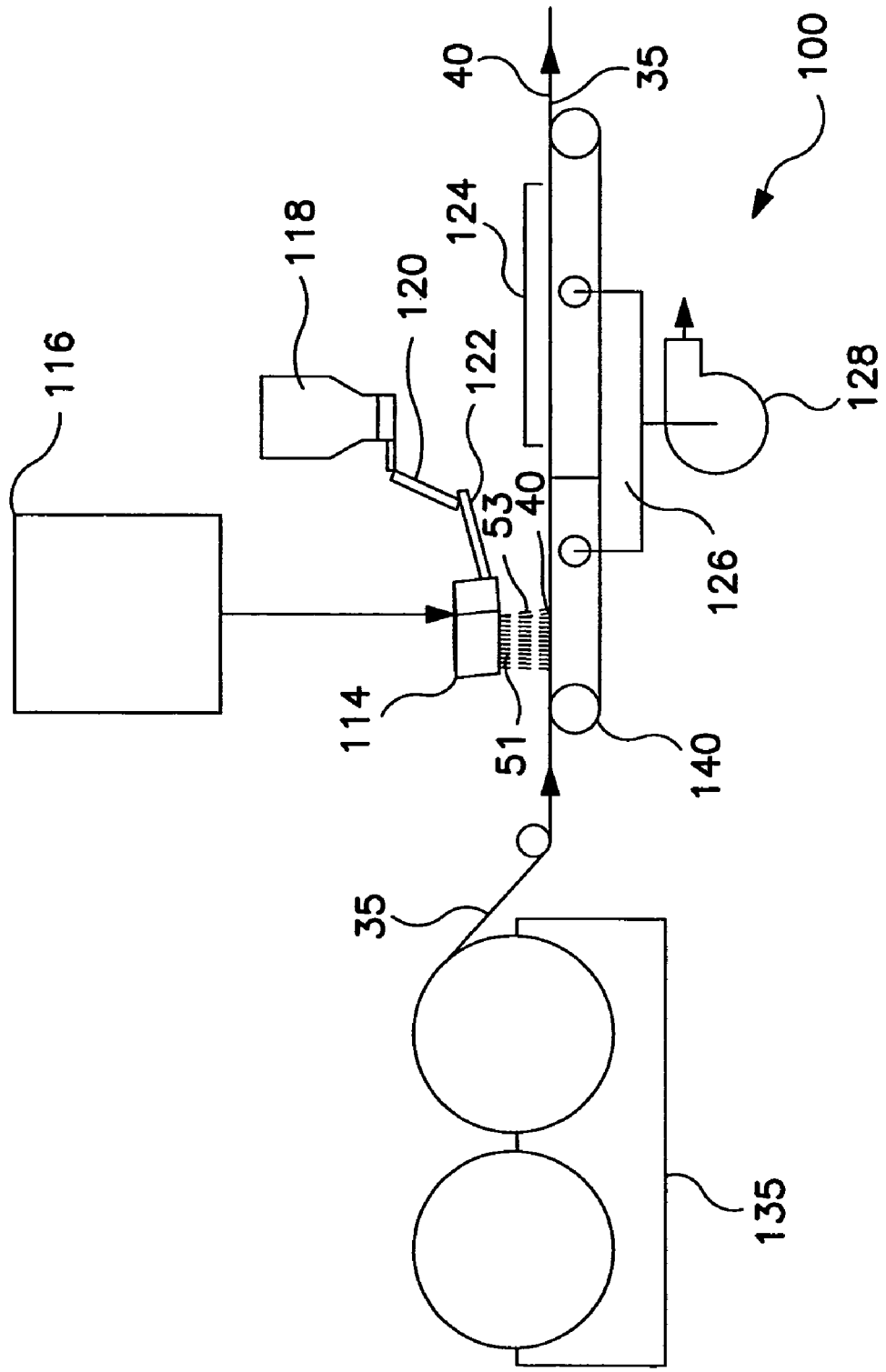
FIG. 5 schematically illustrates an overall process for forming and shaping an absorbent core on a substrate, which can be integrated with a process for assembling the layers of an absorbent article.
Figure 6:
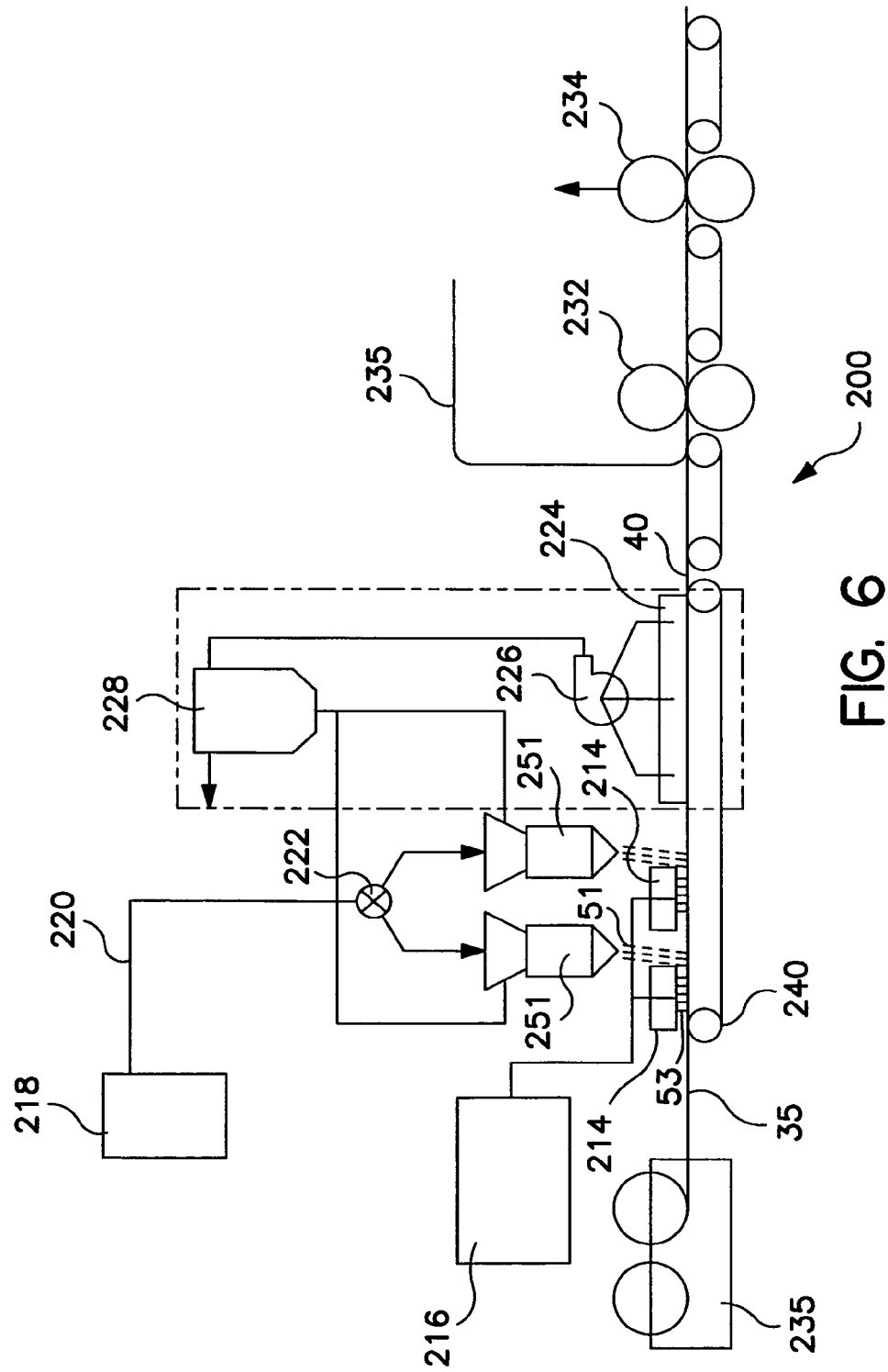
FIG. 6 schematically illustrates an alternative process for forming and shaping an absorbent core on a substrate.

FIGS. 5 and 6 illustrate alternative processes for integrating the superabsorbent particles 51 with the adhesive fibers 53, to form the absorbent core 40 on the substrate 35. In the process 100 of FIG. 5, the superabsorbent particles and adhesive fibers are combined before contacting the substrate. In the process 200 of FIG. 6, the adhesive fibers and superabsorbent particles are applied as alternating layers. Either of these processes may be practiced using controlled adhesive application to shape the absorbent core, as described with respect to FIG. 3, or air jets to shape the adhesive pattern (and the absorbent core) as described with respect to FIG. 4.

Referring to FIG. 5, a substrate 35 is unwound from a roll assembly 135 and is transferred to a conveyor assembly 140 where it passes under a hot melt adhesive applicator 114 which includes a plurality of adhesive nozzles arranged in a row as described above. The adhesive applicator 114 may be disposed perpendicular to the machine direction of substrate 35, or offset at an angle as shown. Adhesive from a grid melter 116 or other source is continuously fed to applicator 114 which applies adhesive fibers 53 to substrate 35, according to any above-described technique.

Superabsorbent particles 51 are continuously fed from a weigh feeder 118, which can be a K-TRON® feeder, through a chute 120 to a distributor or vibrating pan 122. The vibrating pan 122 deposits the superabsorbent particles directly into the air stream which carries the melt blown adhesive fibers 53 to the substrate, or into a separate air stream which carries the superabsorbent particles to the melt blown adhesive fibers. By depositing superabsorbent particles 51 into either air stream, the superabsorbent particles 51 commingle and combine with the adhesive fibers 53 such that superabsorbent particles 51 and adhesive fibers 53 are applied simultaneously to the substrate 35, forming absorbent cores 40.

If the process of FIG. 5 is used in conjunction with the selective adhesive application technique of FIG. 3, then there will be excess superabsorbent particles 51 which do not commingle with adhesive fibers 53 and do not become part of absorbent core 40. In order to form a uniform combination of superabsorbent particles and adhesive fibers across the width of absorbent core 40, it is desirable to continuously channel superabsorbent particles 51 from vibrating tray 122 across the entire width of adhesive applicator 114 which is used to apply adhesive. However, as explained with respect to FIG. 3, adhesive flow from many of the nozzles is periodically interrupted to cause shaping of the absorbent core. The shaping can be controlled by a signaling device (not shown) which sends signals from the conveyor assembly 140 to a controller for adhesive applicator 114. Superabsorbent particles 51 will continue to deposit on adhesive-free regions of substrate 35 which are affected by the adhesive interruptions, resulting in loose superabsorbent particles.

A vacuum box 124 and vacuum pump 128 are provided along conveyor 140 for collection and recycling of loose superabsorbent particles 51. The continuous web of absorbent cores 40 formed on substrate 35 passes vacuum lines 126, through the vacuum box 124, and then to a cutting station (not shown) which severs the moving web into individual absorbent cores 40, each formed on a section of substrate 35. The vacuum box 124 channels the loose superabsorbent particles to a collector for recycling.

Alternatives to a vacuum box 124, such as blowers, vibrating trays or the like, may also be employed to recycle loose superabsorbent particles. Also, if the process of FIG. 5 were instead used in conjunction with the adhesive application technique of FIG. 4, then the air jets used to shape the absorbent core would influence the deposition of superabsorbent particles as well as adhesive fibers and would maintain them in a commingled state. There would be few, if any, loose superabsorbent particles, and a recycling system may not be needed.

FIG. 6 illustrates another process 200 of making an absorbent core 40 by applying alternating layers of adhesive fibers and superabsorbent particles. A substrate layer 35 is unwound from a roll assembly 235 and is transferred to a conveyor assembly 240 where it passes under a plurality of alternating hot melt adhesive applicators 214 and superabsorbent particle dispensers 251. Each hot melt adhesive applicator 214 and particle dispenser 251 may be disposed perpendicular to the machine direction of substrate 35, or offset at an angle. Adhesive from a drum unloader and melter 216 or other source is continuously fed to adhesive applicators 214 which apply adhesive fibers 53 to substrate 35, according to any above-described technique.

Superabsorbent particles 51 are continuously fed from a bulk bag 218 via a pusher line 220, to a divider 222 which allocates the superabsorbent particles to the plurality of dispensers 251. Each dispenser 251 is equipped with a metering mechanism for adjusting the flow rate of superabsorbent particles 51 from the dispenser. Superabsorbent particles 51 are deposited from each dispenser onto substrate 35.

As shown in FIG. 6, adhesive fibers 53 are deposited as a first layer onto substrate 35 from the first applicator 214. Then superabsorbent particles 51 from the first dispenser 251 are deposited as a second layer over the first layer of adhesive fibers 53. Then, adhesive fibers are deposited as a third layer from the second applicator 214. Then, superabsorbent particles are deposited as a fourth layer from the second dispenser 251. The process illustrated in FIG. 6 may be used to form an absorbent core from one to four or more adhesive fiber layers and one to four or more superabsorbent particle layers, depending on the desired basis weight and thickness of the absorbent cores 40 being formed. The order of layers may also be reversed or otherwise altered.

A vacuum box 224 is provided along conveyor 240 for collection and recycling of loose superabsorbent particles 51. The vacuum box 224 is equipped with a suction fan 226 which lifts the loose superabsorbent particles to a cyclone 228, for recycling back to the receiving hopper 218. Other methods of supplying air flow, such as a blower or compressed air, may also be used to recycle the loose superabsorbent particles. The process of FIG. 6 may be used in conjunction with any of the adhesive application techniques discussed with respect to FIGS. 3 and 4. As explained with respect to FIG. 5, if air jets are used to shape the absorbent cores 40, then there may not be any significant amount of loose superabsorbent particles. In this instance, a vacuum box or other recycling system may not be needed.

In the process of FIG. 6, a second substrate 235 is applied over the absorbent cores 40, leaving each absorbent core 40 sandwiched between the layers 35 and 235. The layers 35, 40 and 235 are sealed together with the aid of a nip assembly 232. The entire laminate is then passed to a cutting station 234 which separates the individual absorbent cores 40 which have been formed end-to-end, and also cuts through the layers 35 and 235. Each absorbent core 40 is thus provided between two substrates, in a sandwich structure.

In one embodiment, the absorbent core 40 is not stretchable, or is stretchable to a lesser extent than the substrate layer 35. When the substrate layer 35 is stretched, the absorbent core may either rupture or become partially detached from the substrate layer 35. In another embodiment, the absorbent core 40 can be stretched, without rupture, to at least the same extent as the substrate layer(s) to which it is applied, or to a greater extent. The absorbent core 40 is typically not elastic. Typically, the combination of absorbent core and substrate can be stretched by at least 50%, to at least 150% of an initial length in at least one direction, without rupturing either layer.

If the substrate is an outer cover, the absorbent core need not inhibit stretching of the outer cover. If the substrate is a bodyside liner, the absorbent core need not inhibit stretching of a bodyside liner. The same holds true whether the substrate is a surge layer, spacer layer, or any other layer. The absorbent article is stretchable, and may be elastic. The previous problems associated with absorbent cores preventing the stretchability or elastic recovery of absorbent articles are therefore overcome.

The stretchability of the absorbent core 40 can be determined by a variety of factors, including a) the relatively low modulus of adhesive, b) the relatively low basis weight of adhesive, c) the low percentage of adhesive relative to superabsorbent particles in the absorbent core, and d) the application of the adhesive as fibers, particularly as fine, meltblown fibers. Another contributing factor is the fact that the absorbent core need not contain cellulose fibers, or other fibers which are neither stretchable nor elastic. The absorbent core 40 can be used in a wide variety of personal care absorbent articles and medical absorbent articles, and is particularly useful in absorbent articles that are intended to be stretchable or elastic.

Test Procedures

The following test procedures can be used to measure the properties of the adhesives useful in the absorbent core of the invention.

Viscosity Test

The Viscosity Test is conducted in accordance with ASTM Test Method D3236-88, entitled "Standard Test Method for Apparent Viscosity of Hot Melt Adhesives and Coating Materials," the entire disclosure of which is incorporated herein by reference, with the following parameters. The viscometer used is that made by Brookfield Engineering Laboratories of Middleboro, Mass., U.S.A., as model RVDV III. The spindle number to use in conducting the ASTM Test Method is SC4-27. The sample size should be about 10.5 grams of adhesive. The spindle speed (rpm) is set to a value that results in a torque reading in the range of 20 percent to 80 percent. A reading should be taken every few minutes for about 15 minutes, or until the viscosity values stabilize, after which the final viscosity reading (in centipoises) is recorded.

Some of the exemplary adhesives described above have the following viscosities (centipoise) at the following temperatures.

| Temperature (Degrees Centigrade) | HX 4207-01 Viscosity (cps) | HX 2773-01 Viscosity (cps) | 34-5610 Viscosity (cps) |
|---|---|---|---|
| 121 | 7,925 | 7,437 | 19,100 |
| 135 | 3,887 | 3,587 | 9,462 |
| 149 | 2,155 | 1,990 | 5,412 |
| 163 | 1,300 | 1,197 | 3,275 |
| 177 | 843 | 758 | 2,175 |

Rheology Test

The Rheology Test is used to determine the storage modulus and glass transition temperature of a hot-melt adhesive. The Rheology Test is conducted generally in accordance with ASTM Method D4440-01, entitled "Standard Test Method for Plastics: Dynamic Mechanical Properties Melt Rheology," the entire disclosure of which is incorporated herein by reference to the extent that it is consistent herewith.

The Rheology Test is conducted using an Advanced Rheometric Expansion System (ARES) rheometer, available from TA Instruments of New Castle, Del., U.S.A. The ARES rheometer is equipped with a transducer, available from TA Instruments as model no. 2K FRTN1, and software which is also available from TA Instruments under the tradename ORCHESTRATOR, version 6.5.1. The ARES rheometer also uses 8 mm parallel plates, which are available from TA Instruments.

The 8 mm plates are installed in the ARES rheometer by first using the stage control buttons of the rheometer to raise the stage to thereby provide sufficient room for installing the plates. With motor on and in dynamic mode, the upper and lower plates are mounted on the actuator shafts of the rheometer. The torque and normal force are each zeroed by pressing the XDCR ZERO button on the user interface. The stage is then lowered to a point at which the plates are close but not touching. Using the ZERO FIXTURE button in the set gap/instrument control function under the control menu of the software, the plates are brought together and the zero point determined for the plates. The stage is then raised to separate the plates a sufficient distance for loading a test sample therebetween.

The adhesive sample to be tested should be larger than each 8 mm plate (e.g., as initially formed or otherwise cut from a larger sample), and should have a thickness of at least 2 mm. The adhesive sample is placed on the lower plate and the stage is lowered until a compressive force of approximately 50 to 100 grams is generated. The adhesive sample is then heated to its softening point. The gap reading on the user interface should be between 0.5 and 5 mm, and more suitably between 1 and 3 mm. If necessary, the stage can be raised or lowered to adjust the gap. Excess adhesive (e.g., exterior of the peripheral edges of the plates) is removed using a hot soldering iron.

The test conditions to be specified in the software are as follows:

The temperature control is set for that associated with using liquid nitrogen.
Geometry is set to 8 mm plates
Read Test Fixture Gap: "ON"
Testing Mode: Dynamic Temperature Ramp
Frequency: 6.28 radians/second
Ramp Rate: 3 degrees/minute
Initial Temperature: −20° C.
Final Temperature: 100° C.
Strain: 0.5%
Time per measure: 5 seconds
Auto Tension Adjustment: "ON"
Initial Static Force: 300 grams
Auto Tension Sensitivity-300 grams In the ORCHESTRATOR software, under the Control menu, select EDIT/START TEST and then select BEGIN TEST to start the test. Once the sample has been tested, the software is used to plot the storage modulus (G'), in dynes/square centimeter, on the primary y-axis; tan delta on the secondary y-axis, and temperature, in degrees Celsius, on the X-axis. The storage modulus (G') at 25° C. for the adhesive sample is determined from the plot. The glass transition temperature (Tg) is the temperature (on the plot) at which the maximum peak occurs on the tan delta versus temperature curve.

Some of the exemplary adhesives described above have the following storage modulus (G') at 25° C., and the following glass transition temperatures, ° C.

| Adhesive | G' at 25° C. (×10⁵ dynes/cm²) | Tg (° C.) |
| --- | --- | --- |
| HX 4207-01 | 5.26 | 20.0 |
| HX 2773-01 | 4.34 | 19.2 |
| H2525A | 9.8 | 20.6 |
| 34-5610 | 5.0 | 12.5 |
| 34-447A | 0.971 | −8.84 |

The following test procedure determines whether or not an absorbent article, or layer component, is "stretchable" or "elastic" as described above.

Elongation and Recovery Test

The Elongation and Recovery Test is a three cycle elongation and recovery test used to measure the elongation and recovery characteristics of an absorbent article, and more particularly of a test specimen comprising an absorbent core secured to one or more substrates or other components. In particular, the Test may be used to determine what effect, if any, securing the absorbent core to the substrate(s) has on the elongation and recovery characteristics thereof. The test measures load values of a test sample placed under a particular amount of strain (e.g., elongated to a particular elongation). Such load values are determined during both the elongation and recovery phases of the Test, and during each of the three cycles. The recovery of each test sample is determined by the degree of permanent elongation after the load value drops to 3.3 grams-force (gf) per inch of sample width during the recovery phase. The Test is conducted on the specimen (e.g., the absorbent core secured to the substrate(s)) as well as on the substrate(s) independent of the absorbent core and the results are compared.

Sample Preparation

Six samples of the test specimen should be subjected to the Elongation and Recovery Test, three samples of the full specimen and three samples of the substrate(s) independent of (e.g., separated from) the absorbent core of the specimen, and the results for each set of three samples should be averaged. Each sample should be approximately 3 inches (76 mm) wide by at least 5 inches (127 mm) long, and more preferably at least 6 inches (152 mm) long. Where the specimen is taken from a manufactured article having a width greater than 3 inches, the samples should be cut from the midline of the specimen, i.e., samples which include the widthwise edges of the article should be avoided to reduce the risk that edge effects may cause inconsistent results in testing.

The sample should be free from attachment to any other article components that may be present, such as leg or waist elastic structures, impermeable outer covers or liners (if not manufactured to be secured to the absorbent composite), etc., at least in the region to be used as a sample. Unrelated components can be present at the longitudinal ends of the sample (e.g., at the ends which are to be held within grips of the tester, as described later herein) only under the following circumstances: 1) they do not add substantially to the thickness of the sample and do not cause the effective gage length to increase (i.e., a sample end inside a grip is placed under tension because of irregular thickness of the sample), and 2) they do not affect the appearance or behavior of the region of the sample being tested (e.g., causing the sample to be rippled or contracted, or inhibiting the elongation of any part of the sample to be tested).

Where a given test specimen will not permit samples of the desired dimensions (e.g., 3 inches wide by at least 5 inches long) to be prepared, the length of the sample selected should be as long as possible while allowing sufficient material at the ends of the same (e.g., at least one-half (½) inch (13 mm) for gripping in the tensile tester). All samples of a given specimen must be tested at the same length. The gauge separation is set to maintain an aspect ratio of at least 1:1, suitably 1.33:1, relative to the sample length. Samples having a length of one inch or less or a width of one inch or less should not be used.

Where the samples are to be taken from an already manufactured article, the substrate(s) to which the absorbent core is secured must be separated from the absorbent core for testing. This may be achieved by one of the following methods. Care should be taken to avoid stretching the substrate(s) during separation. The article (e.g., substrate(s) and absorbent core secured thereto) from which the substrate(s) is/are to be taken should be cut to the desired sample dimensions prior to conducting one of the following to separate the substrate(s) from the absorbent core.

1) The article may be frozen, such as with liquid nitrogen, to permit the substrate(s) to be separated from the absorbent composite; or 2) Depending on adhesive chemistry, the article may be treated with a solvent selected to dissolve the adhesive composition of the absorbent core without affecting the structure or properties of the substrate(s).

Where an absorbent core of the specimen to be tested is secured to more than one substrate used to support or enclose the absorbent core (e.g., one to each major face of the absorbent core), the substrates should be overlaid with each other (in the same relative orientation as in the article) without elongating any of the substrates or other components, and tested together as a single sample.

Test Apparatus and Materials

The following test apparatus and materials are used to conduct the Elongation and Recovery Test.

1) Constant Rate of Extension (CRE) tensile tester: MTS tensile tester model SYNERGIE 200 TEST BED, available from MTS Systems Corporation, Research Triangle Park, N.C., U.S.A.

2) Load cells: A suitable cell selected so that the majority of the peak load values fall between the manufacturer's recommended ranges of the load cell's full scale value. Load cell Model 100N available from MTS Systems Corporation is preferred.

3) Operating software and data acquisition system: MTS TESTWORKS for Windows software version 4, available form MTS® Systems Corporation.

4) Grips: pneumatic-action grips, top and bottom, identified as part number 2712-003 available from Instron Corporation, Canton, Mass., U.S.A.

5) Grip faces: 25 mm by 100 mm.

Test Conditions

Reasonable ambient conditions should be used for sample testing, such as 73+/−2° F. (about 23° C.) and a relative humidity of 50+/−2%. If the samples are stored under substantially different conditions, the samples should be measured after they equilibrate to laboratory conditions.

The instruments used should be calibrated as described in the manufacturer's instructions for each instrument.

The tensile tester conditions are as follows:
Break sensitivity: 60%
Break threshold: 200 grams-force
Data acquisition rate: 100 Hz
Preload?: No
Slowdown extension: 0 mm
Test speed: 508 mm/min.
Full scale load: 10,000 grams-force Gage length: 4 inches (102 mm)
Number of cycles: 3

Test Method

Calibrate the load cell using the TESTWORKS software at the beginning of each work session. Using the tensile frame pushbutton controls for cross-head position, move the grips to provide a gage length (distance between grips) of 4 inches (102 mm). Calibrate the software to this initial gage length. Place the sample to be tested lengthwise so that it is centered between the grips, held in a centered position within each grip, and oriented correctly (e.g., with the widthwise dimension running transverse to the length between the grips), e.g., with the vertical (e.g., side) edges of the sample perpendicular to the grip faces. Close the grips on the sample, holding the sample in such a way as to minimize slack in the sample without placing the sample under tension.

Ensure that the load at this point is less than ±3.3 grams per inch of sample width. If the load is greater than 3.3 grams per inch width, release the lower grip and zero the load cell. Re-close the lower grip, again ensuring that the sample is neither under tension nor buckled with excessive slack. Continue checking the starting load and following the above procedure until the starting load is within the desired range.

Run the three cycle test using the above parameters by clicking on the RUN button. When the test is complete, save the data to a sample file. Remove the sample from the grips. Run the above procedures for the remaining samples of a given specimen. The data for all samples should be saved to a single file.

Report the data for each sample as follows: Average peak load at 20, 40, 60, 80 and 100% elongation; average percent set following each cycle; and average percent recovery following each cycle. A specimen with a peak load that exceeds the limits of the load cell (~10,000 grams-force) should have a peak load listed as >10,000 grams-force. The average calculation for that sample should use 10,000 grams-force as the peak load for that specimen, with a notation made that the average is conservative (low) due to rounding down at least one peak load level to 10,000 grams-force.

The peak load should be normalized by dividing by the width of the sample to determine a normalized peak load per one inch of sample width. The normalized peak load of the specimen is considered to be the average normalized peak load during the first elongation cycle. Percent set and recovery values should be determined by recording the gage length (distance between grip faces) at which the load value on the recovery phase of each cycle drops to 3.3 grams-force per inch of sample width. For samples 3 inches in width, this is a load value of 10 grams-force.

The percent set of each sample is calculated by the following formula:

$$\frac{\text{gage length when load value of 3.3 grams-force per inch of sample width is reached on the last recovery cycle} - \text{starting length}}{\text{starting gage length}} \times 100$$

The percent recovery of each sample is calculated by the following formula:

100−percent set.

The above Test procedures are conducted first for all of the samples of the full specimen (absorbent core secured to the substrate(s)), and again for all of the samples of the substrate(s) independent of the absorbent core of the specimen. The effect of securing the absorbent core to the substrate(s) is determined as follows:

(percent recovery of the full specimen divided by the percent recovery of the substrate(s))×100.

Test for Measuring P/EL and MDFME

X-ray and image analysis are used in conjunction to determine the perimeter to edge length ratio as well as the distance the standard deviation from the mean edge. Together, these values indicate the degree of convolution of an edge of an absorbent composite as well as how random the perimeter is with respect to the average edge position.

Sample Preparation

Carefully remove the absorbent core from the diaper with a minimum of disturbance, while maintaining the core in contact with any tissue or nonwoven layers to which the absorbent core may be adhered or which serve to maintain the integrity of the absorbent core. Then place the absorbent core and adjacent nonwoven or tissue layers into the x-ray apparatus. Alternatively, if the absorbent core cannot be readily removed from the diaper without significant disruption of the absorbent and adjacent layers, then place the intact diaper into the x-ray and analyze the entire structure. If there are layers present in the diaper which contain high atomic number constituents that will preferentially absorb x-rays and hinder analysis of the absorbent core (e.g. $CaCl_2$ or $TiO_2$ can be present in significant amounts in film layers), then remove the layers containing the high atomic number constituents and x-ray this layer or layers alone and digitally subtract their effect from that of the image of the entire diaper.

Test Apparatus and Materials

The x-ray method of determining the mass of an absorbent, whether in the wet or dry state, is generally known in the art and is described for wet and dry absorbents in, for example, an article entitled "Fluid Distribution: comparison of X-ray Imaging Data" by David F. Ring, Oscar Lijap and Joseph Pascente in Nonwovens World magazine, summer 1995, pages 65-70. Analysis of the resulting grayscale image can then be accomplished using software such as Matlab, available through Mathworks, Inc. (Natick, Mass.).

Test Conditions

Reasonable ambient conditions should be used for sample testing, such as 73+/−2 degree Fahrenheit (about 23 degrees Celsius) and a relative humidity of 50+/−2 percent. If the samples are stored under substantially different conditions, the samples should be measured after they equilibrate to laboratory conditions.

The x-ray and image capture instruments used should be calibrated as described in the manufacturer's instructions for each instrument. The acquired x-ray image should have at minimum 30 gray levels (8 bit; 0-255 scale) of contrast, which will be dependent on the equipment power settings. Any x-ray instrumentation with sufficient resolution and field of view should be adequate. The grayscale image of the absorbent core obtained from the camera is then analyzed according to the following method.

Image Analysis Procedure

Figure 7:
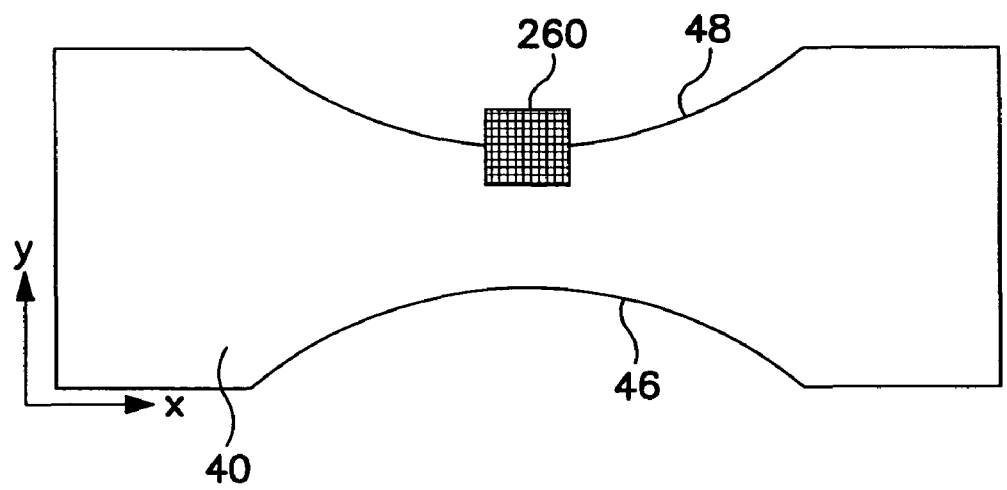
FIG. 7 schematically illustrates a gray scale image of an absorbent pad and placement of the Region Of Interest for determining a Perimeter to Edge Length ration and Mean Distance from Mean Edge.

The grayscale image obtained from the x-ray procedure described above is then analyzed. FIG. 7 shows diagrammatically a grayscale image of an absorbent core. The total field assessed or region of interest (ROI) in order to determine the Perimeter to Edge Length ratio or the Mean Deviation from the Mean Edge is 48.1 mm in the x dimension and 48.1 mm in the y dimension. FIG. 7 illustrates the placement of the ROI 260 in relation to the absorbent in order to obtain a flat edge region to analyze. The ROI of FIG. 7 is meant only to show the general spatial relationship between the absorbent edge in the image and the ROI. The ROI and the number of elements in the ROI are defined below. It should also be understood that other edge regions can also be analyzed, provided that they are flat and do not have significant curvature which could interfere with the analysis. While a straight edge makes this calculation straightforward, departure or curvature measurements could also be made with regard to the nominal curvature of a region which would embody the local edge. In these cases where there is no sufficiently straight portion to the material edge to perform the above analysis, one may approximate a curved edge by end-to-end line segments no shorter than 1 cm along the perimeter. The edge length will then be the total length of these line segments. The deviations from the edge can be calculated using the standard point to line distance formula of all boundary points to their nearest line segment. The distance from the line $Ax+By+C=0$ to point$(x2,y2)$ is $D=(Ax2+By2+C)/(+/-sqrt(A^2+B^2))$. In any case, the size of the ROI is to remain fixed. Resolution, or the size of individual pixels which construct the total field of view, is 0.36 mm in both length and width, to give a total of 17689 pixels assessed.

Figure 8A:
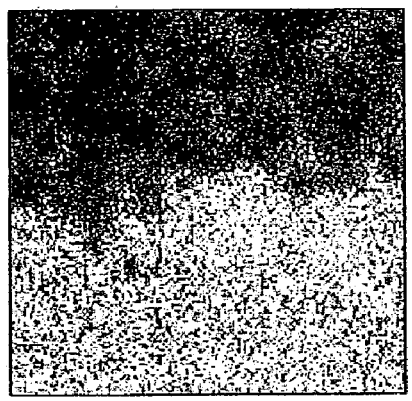
FIG. 8 shows a gray scale image for a Region Of Interest for an in-line formed edge and a cut edge, along with corresponding segmented images.

The absorbent core and substrates were imaged using the x-ray technique described above. The grayscale image is then analyzed according to the following method. FIG. 8a is an ROI taken from a grayscale image of an absorbent core formed on-line in between two substrates. The ROI is then segmented using an intensity threshold calculated as the average of the mean gray level of absorbent core plus substrates (from the ROI edge farthest in the absorbent core plus substrates; i.e. the upper edge of FIG. 8a) and the mean background gray level which is substrates only (from the ROI edge farthest outside the substrates plus absorbent; i.e. the lower edge of FIG. 8a).

Figure 8B:
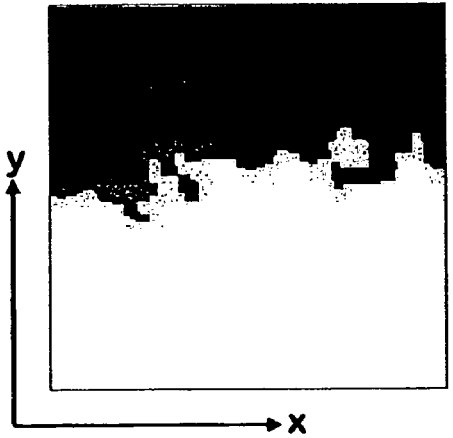
Figure 8C:
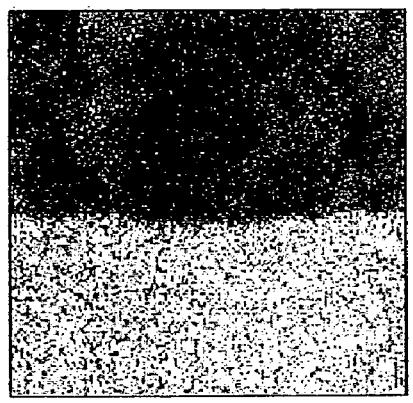
Figure 8D:
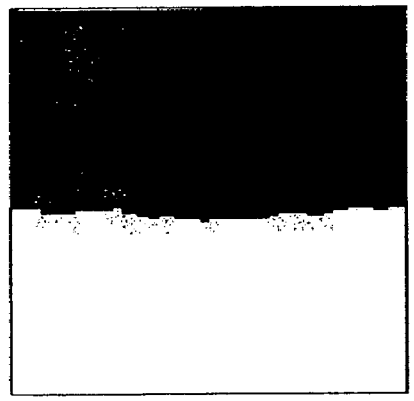

The segmented image is morphologically opened and closed with 3×3 kernels to remove noise and smooth some high frequency structures in the image. The segmented image corresponding to FIG. 8a is shown in FIG. 8b. A similar grayscale image for an absorbent core with a cut edge is shown in FIG. 8c along with the corresponding segmented image in FIG. 8d. The boundary pixels in the segmented images are those that are at the single interface between the largest white and black regions of the binary image. The individual boundary coordinates are used to calculate the Perimeter (P) along the edge which is then compared to the Edge Length (EL) which is the length of the ROI parallel to the absorbent edge. The perimeter per edge length (P/EL) is a measure of how convoluted a boundary is, with a Euclidean line having a P/EL=1, where a rough boundary will have larger P/EL values. The individual boundary coordinates are furthermore used to determine the average boundary departure into the absorbent material and background regions from the Mean Edge (ME) position. When the edge is oriented parallel to the x-axis, the ME position is determined by taking the average of all the y boundary positions.

The Mean Deviation From the Mean Edge (MDFME) is then determined by taking the average of the absolute difference between the boundary and the mean edge at each position across the x axis of the ROI. The following equation shows the MDFME:

$$MDFME = \frac{\sum_x |y - ME|}{n}$$

Samples which are cut will have a lower MDFME than formed samples, having magnitudes which approach 0.

Using this method, the following results were obtained for an absorbent core and substrate with the indicated composition, having cut versus formed (uncut) edges:

| Parameter | Cut Edge | Formed Edge |
|---|---|---|
| P/EL | 1.08 | 8.49 |
| MDFME | 0.47 mm | 2.26 mm |

The absorbent core and substrate tested above had the following composition:
Total basis weight: 450 gsm (grams per meter squared)
SAM Content and Type: 410 gsm of SXM 9394 available from Stockhausen, Inc. with offices in Greensboro, N.C.
Adhesive Content and Type: 20 gsm of 34-5610 adhesive available from National Starch.
Tissue: 20 gsm available from American Tissue.

It should be recognized that other substrates, superabsorbents and adhesives can all be used to give substantially similar results. For example, other substrates (whether stretchable or non-stretchable) such as nonwovens including spunbonds, meltblown and combinations of spunbond and meltblown as well as nonwovens including stranded elastics are all part of the invention.

These data show that the formed edge has a higher P/EL ratio, indicating that it is a rougher edge (i.e. not as cleanly defined) as compared to the cut edge which has a P/EL ratio close to one. The MDFME similarly shows that the formed edge has a higher deviation from the mean edge, again indicating that the formed edge is not as cleanly defined as the cut edge, thus allowing a distinction to be made between a pad formed on-line as compared to one which is die cut in order to define the shape.

While the embodiments of the invention described herein are presently preferred, various modifications and improvements can be made without departing from the spirit and scope of the invention. The scope of the invention is indicated by the appended claims, and all changes that fall within the meaning and range of equivalents are intended to be embraced therein.

We claim:

1. An absorbent article, comprising:
a liquid-permeable bodyside liner;
a liquid-impermeable outer cover; and
a shaped absorbent core between the bodyside liner and the outer cover;
the absorbent core comprising about 40-99% by weight superabsorbent particles and about 1-60% by weight adhesive fibers, wherein the adhesive fibers include a tackifier;
the absorbent core having a front end, a rear end and two lateral sides;
wherein the lateral sides of the absorbent core have a P/EL greater than or equal to 1.25 and a MDFME greater than or equal to 0.7 mm; and wherein the absorbent core comprises a central region and two end regions, and at least one of the end regions is wider than the central region.

2. The absorbent article of claim 1, wherein the absorbent core is adhesively attached to a substrate layer along substantially an entire surface of the absorbent core.

3. The absorbent article of claim 2, wherein the substrate is stretchable.

4. The absorbent article of claim 2, wherein the substrate is elastic.

5. The absorbent article of claim 2, wherein the substrate comprises the outer cover.

6. The absorbent article of claim 2, wherein the substrate comprises the bodyside liner.

7. The absorbent article of claim 2, wherein the substrate is selected from the group consisting of a fibrous nonwoven web, and combinations including a fibrous nonwoven web.

8. The absorbent article of claim 1, wherein the absorbent core comprises about 80-98% by weight superabsorbent particles and about 2-20% by weight adhesive fibers.

9. The absorbent article of claim 1, wherein the absorbent core further comprises cellulose fibers.

10. The absorbent article of claim 1, wherein the adhesive fibers are formed of an adhesive having a viscosity less than about 10,000 centipoise at a temperature of 204° C.

11. The absorbent article of claim 10, wherein the adhesive has a viscosity of less than about 10,000 centipoise at a temperature of 182° C.

12. The absorbent article of claim 11, wherein the viscosity is about 1,000-8,000 centipoise.

13. The absorbent article of claim 1, wherein the adhesive fibers are formed of an adhesive having a storage modulus of less than or equal to about $1.0 \times 10$ dynes/cm$^2$ at 25° C.

14. The absorbent article of claim 1, wherein the adhesive fibers are formed of an adhesive having a glass transition temperature of about −25° C. to about 25° C.

15. The absorbent article of claim 1, wherein the superabsorbent particles comprise a cationic polymer and an anionic polymer.

16. The absorbent article of claim 1, wherein the absorbent core has a dumbbell shape.

17. The absorbent article of claim 1, wherein the absorbent core has an I-beam shape.

18. The absorbent article of claim 1, wherein the absorbent core has a T-shape.

19. The absorbent article of claim 1, wherein the absorbent core has an hour-glass shape.

20. The absorbent article of claim 1, wherein the absorbent core is adhesively attached to two substrate layers along substantially entire surfaces of the absorbent core.

21. The absorbent article of claim 1, wherein both end regions of the absorbent core are wider than the central region.

22. An absorbent article, comprising:
a stretchable substrate layer; and
a shaped absorbent core comprising a combination of about 40-99% by weight superabsorbent material and about 1-60% by weight adhesive fibers, adhesively attached to the substrate layer along substantially an entire surface of the absorbent core, wherein the adhesive fibers include a tackifier;
the absorbent core having a length equal to a length of the substrate layer and a width less than a width of the substrate layer along the entire length of the absorbent core;
wherein the absorbent core combined with the substrate layer is stretchable;
wherein the absorbent core has lateral sides which have laterally extending peaks and valleys defining a P/EL greater than or equal to 1.25 and a MDFME greater than or equal to 0.7 mm; and
wherein the absorbent core comprises a central region and two end regions, and at least one of the end regions is wider than the central region.

23. The absorbent article of claim 22, wherein the substrate layer is elastic.

24. The absorbent article of claim 22, wherein the absorbent article is elastic.

25. The absorbent article of claim 22, wherein the substrate layer comprises a bodyside liner.

26. The absorbent article of claim 22, wherein the substrate layer is selected from the group consisting of a fibrous nonwoven web, and combinations including a fibrous nonwoven web.

27. The absorbent article of claim 22, wherein the substrate layer comprises a spacer layer.

28. The absorbent article of claim 22, wherein the substrate layer comprises an outer cover.

29. The absorbent article of claim 22, wherein both end regions of the absorbent core are wider than the central region.

30. The absorbent article of claim 22, wherein the absorbent core comprises about 40-99% by weight superabsorbent particles and about 1-60% by weight adhesive fibers.

31. The absorbent article of claim 22, wherein the absorbent core comprises about 80-98% by weight superabsorbent particles and about 2-20% by weight adhesive fibers.

32. The absorbent article of claim 22, wherein the absorbent core further comprises cellulose fibers.

33. The absorbent article of claim 22, comprising two of the stretchable substrate layers adhesively attached to opposing surfaces of the absorbent core.

34. The absorbent article of claim 22, wherein the article is a personal care absorbent article or a medical absorbent article.

35. An absorbent article, comprising:
a stretchable substrate layer; and
a shaped absorbent core adhesively attached to the substrate layer; the absorbent core comprising about 40-99% by weight superabsorbent particles and about 1-60% by weight adhesive fibers and having a front end, a rear end, and two lateral sides, wherein the adhesive fibers include a tackifier;
wherein the lateral sides of the absorbent core have a P/EL greater than or equal to 1.25 and a MDFME greater than or equal to 0.7 mm; and
wherein the absorbent core comprises a central region and two end regions, and at least one of the end regions is wider than the central region.

36. The absorbent article of claim 35, wherein the lateral sides have laterally extending peaks and valleys defining a P/EL greater than or equal to 4.0 and a MDFME greater than or equal to 1.0 mm.

37. The absorbent article of claim 35, wherein the lateral sides have laterally extending peaks and valleys defining a P/EL greater than 8.0 and a MDFME greater than 2.0 mm.

38. The absorbent article of claim 35, wherein the substrate layer is elastic.

39. The absorbent article of claim 35, wherein the absorbent article is elastic.

40. The absorbent article of claim 35, wherein the absorbent article comprises about 80-98% by weight superabsorbent particles and about 2-20% by weight adhesive fibers.

41. The absorbent article of claim 35, wherein the absorbent core further comprises cellulose fibers.

42. The absorbent article of claim 35, comprising two of the stretchable substrate layers adhesively attached to opposing surfaces of the absorbent core.

43. The absorbent article of claim 35, wherein the article is a personal care absorbent article.

44. The absorbent article of claim 35, wherein the article is a medical absorbent article.

45. The absorbent article of claim 22, wherein the tackifier comprises at least one of the group consisting of petroleum distillates, rosins, rosin esters, terpenes and combinations thereof.

* * * * *